(12) United States Patent
Cascallo Piqueras et al.

(10) Patent No.: US 8,974,777 B2
(45) Date of Patent: Mar. 10, 2015

(54) ADENOVIRUS WITH MUTATIONS IN THE ENDOPLASMIC RETICULUM RETENTION DOMAIN OF THE E3-19K PROTEIN AND THEIR USE IN CANCER TREATMENT

(75) Inventors: Manel Maria Cascallo Piqueras, Barcelona (ES); Alena Gros, Barcelona (ES); Ramon Alemany Bonastre, Barcelona (ES)

(73) Assignee: Institut CataláD'oncologia (ES)

( * ) Notice: Subject to any disclaimer, the term of this patent is extended or adjusted under 35 U.S.C. 154(b) by 442 days.

(21) Appl. No.: 12/557,031

(22) Filed: Sep. 10, 2009

(65) Prior Publication Data
US 2010/0124546 A1 May 20, 2010

Related U.S. Application Data

(63) Continuation of application No. PCT/EP2008/052960, filed on Mar. 12, 2008.

(30) Foreign Application Priority Data

Mar. 14, 2007 (ES) .................................. 200700665

(51) Int. Cl.
*C12N 7/01* (2006.01)
*A61K 48/00* (2006.01)
*C12N 15/861* (2006.01)
*A61P 35/00* (2006.01)

(52) U.S. Cl.
USPC ....... 424/93.2; 435/320.1; 435/69.1; 435/455

(58) Field of Classification Search
None
See application file for complete search history.

(56) References Cited

U.S. PATENT DOCUMENTS

| 6,096,718 | A * | 8/2000 | Weitzman et al. | ........... 514/44 R |
| 2004/0072228 | A1 * | 4/2004 | Glynne et al. | ..................... 435/6 |
| 2006/0062764 | A1 * | 3/2006 | Police et al. | ................. 424/93.2 |
| 2006/0281073 | A1 * | 12/2006 | Monaci et al. | ..................... 435/5 |

OTHER PUBLICATIONS

Cascallo et al, Systemic Toxicity-Efficacy Profile of ICOVIR-5, a Potent and Selective Oncolytic Adenovirus Based on the pRB Pathway, Molecular Therapy vol. 15 No. 9, 1607-1615 Sep. 2007.*
Marinheiro et al, A naturally occurring human adenovirus type 7 variant with a 1743 bp deletion in the E3 cassette, Journal of General Virology (2011), 92, 2399-2404.*
Kirn et al, Clinical research results with dl1520 (Onyx-015), a replication-selective adenovirus for the treatment of cancer: what have we learned?, Gene Therapy (2001) 8, 89-98.*
Sester et al, Conserved Amino Acids within the Adenovirus 2 E3/19K Protein Differentially Affect Downregulation of MHC Class I and MICA/B Proteins, The Journal of Immunology, 2010, 184: 255-267.*
Deryckere et al, Early Region 3 of Adenovirus Type 19 (Subgroup D) Encodes an HLA-Binding Protein Distinct from That of Subgroups B and C. Journal of Virology, May 1996, p. 2832-2841.*
Fu et al, Determinants of the endoplasmic reticulum (ER) lumenal-domain of the Adenovirus serotype 2 E3-19K protein for association with and ER-retention of major histocompatibility complex class I molecules. Mol Immunol. Jan. 2011; 48(4): 532-538.*
Teasdale et al, Signal-Mediated Sorting of Membrane Proteins Between the Endoplasmic Reticulum and the Golgi Apparatus., Annu. Rev. Cell Dev. Biol. (1996) 12:27-54.*
Jackson et al., Identification of a consensus motif for retention of transmembrane proteins in the endoplasmic reticulum, The EMBO Journal, vol. 9, No. 10, pp. 3153-3162 (1990).*
Raki et al Combination of gemcitabine and Ad5/3-D24, a tropism modified conditionally replicating adenovirus, for the treatment of ovarian cancer, Gene Therapy (2005) 12, 1198-1205.*
Paabo, et al., a Short Sequence in the Cooh-Terminus Makes an Adenovirus Membrane Glycoprotein a Resident of the Endoplasmic Reticulum, Cell, vol. 50. 311-317, Jul. 17, 1987.
Pahl, et al., Activation of Transcription Factor Ne-Kb by the Adenovirus E3/19K Protein Requires its Er Retention, the Journal of Cell Biology, vol. 132, No. 4, Feb. 1996, 511-522.
Gabathuler, et al., the Endoplasmic Reticulum Retention Signal of the E3/19K Protein of Adenovirus Type 2 Consists of Three Separate Amino Acid Segments at the Carboxy Terminus, the Journal of Cell Biology, vol. 111, Nov. 1990 1803-1810.
Gabathuler, et al., Requirements for the Association of Adenovirus Type 2 E3/19K Wild-Type and Mutant Proteins with Hla Antigens, Journal of Virology, vol. 64 No. 8, Aug. 1990, 3679-3685.
Hermiston, et al., the Discovery and Development of Selectively Replicating Adenoviruses as Anticancer Agents, Tumor Targeting (2000) 4, 218-224.
Yan, et al., Developing Novel Oncolytic Adenoviruses Through Bioselection, Journal of Virology, vol. 77, No. 4, Feb. 2003, 2640-2650 11.
Alemany, et al., "Replicative Adenoviruses for Cancer Therapy," Nature Biotechnology, vol. 18, Jul. 2000.
Alemany, Ramon, "Designing Adenoviral Vectors for Tumor-Specific Targeting," Methods in Molecular Biology, Gene Therapy of Cancer, vol. 542, Chapter 2, pp. 57-74 (2009).
Alemany, Ramon, "Conditionally Replicating Adenoviruses for Cancer Treatment," Chapter 15: Cancer Gene Therapy, 235-249 Humana Press (2005).
Barnett, et al., "Targeted Adenoviral Vectors," Biochimica et Biophysica Acta, 1575 (2002) 1-14. p.
Cascallo, et al., "Systemic Toxicity-Efficacy Profile of Icovir-5, a Potent and Selective Oncolytic Adenovirus Based on the pRB Pathway," Molecular Therapy, vol. 15, no. 9, 1607-1615, Sep. 2007.
Fueyo, et al., "A Mutant Oncolytic Adenovirus Targeting the Rb Pathway Produces Anti-Glioma Effect in Vivo," Oncogene (2000) 19, 2-12.

(Continued)

*Primary Examiner* — Maria Marvich
(74) *Attorney, Agent, or Firm* — Banner & Witcoff, Ltd.

(57) ABSTRACT

The present invention relates to an adenovirus wherein said adenovirus replicates and it contains a mutation in the endoplasmic reticulum retention domain of E3-19K, and to the use of said mutant in treating cancer. Said mutant virus may also contain other mutations and insertions of DNA sequences used to confer selectivity and antitumor potency. The invention has application in the field of cancer therapy.

14 Claims, 12 Drawing Sheets

(56) References Cited

OTHER PUBLICATIONS

Heise, et al., "An Adenovirus E1A Mutant that Demonstrates Potent and Selective Systematic Anti-Tumoral Efficacy," Nature Medicine, vol. 6, No. 10, Oct. 2000.

Krasnykh, et al., "Genetic Targeting of Adenoviral Vectors," Molecular Therapy vol. 1, No. 5, May 2000. El].

Mizuguchi, et al., "Targeted Adenovirus Vectors," Human Gene Therapy, 15:1034-1044 (Nov. 2004).

Suzuki, et al., "A Conditionally Replicative Adenovirus with Enhanced Infectivity Shows Improved Oncolytic Potency," Clinical Cancer Research, vol. 7, 120-126, Jan. 2001.

Flomenberg, Phyllis, et al.,"Human Adenovirus-Specific CD8 T-Cell Responses are not Inhibited by E3-19K in the Presence of Gamma Interferon," Journal of Virology, Sep. 1996, pp. 6314-6322, vol. 70, no. 9, American Society for Microbiology.

* cited by examiner

Figure 4

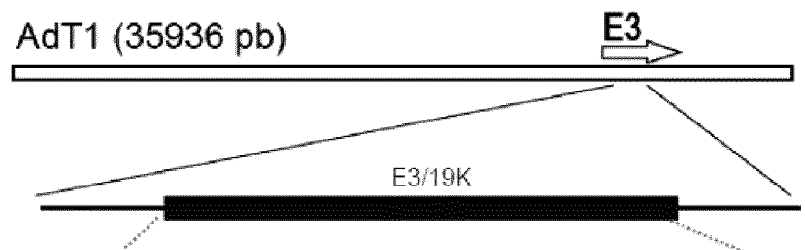

Ad5#28729  SEQ ID NO: 1
ATGATTAGGTACATAATCCTAGGTTTACTCACCCTTGCGTCA
GCCCACGGTACCACCCAAAAGGTGGATTTTAAGGAGCCAGCC
TGTAATGTTACATTCGCAGCTGAAGCTAATGAGTGCACCACT
CTTATAAAATGCACCACAGAACATGAAAAGCTGCTTATTCGC
CACAAAAACAAAATTGGCAAGTATGCTGTTTATGCTATTTGG
CAGCCAGGTGACACTACAGAGTATAATGTTACAGTTTTCCAG
GGTAAAAGTCATAAAACTTTTATGTATACTTTTCCATTTTAT
GAAATGTGCGACATTACCATGTACATGAGCAAACAGTATAAG
TTGTGGCCCCCACAAAATTGTGTGGAAAACACTGGCACTTTC
TGCTGCACTGCTATGCTAATTACAGTGCTCGCTTTGGTCTGT
ACCCTACTCTATATTAAATACAAAAAGCAGACGCAGCTTTAT
TGAGGAAAAGAAAATGCCTTAA    Ad5#29211

Mutation 445-A present in AdT1
Adenine insertion after nucleotide 445 E3-19K cDNA generates a
frame shift (changes AA sequence and truncates the protein):

SEQ ID NO: 3
         Lys Ser Arg Arg Ser Phe Ile Glu Glu Lys Lys Met Pro STOP
Adwt  AAA AGC AGA CGC AGC TTT ATT GAG GAA AAG AAA ATG CCT TAA
AdT1  AAA AAG CAG ACG CAG CTT TAT TGA GGA AAA GAA AAT GCC TTA A
         Lys Lys Gln Thr Gln Leu Tyr

SEQ ID NO: 2

Plaque assay with viruses containing the 445-A mutation and unable to bind MHC-I (A)

Adwt

AdT1

SEQUENCE LISTING

<160> NUMBER OF SEQ ID NOS: 8

<210> SEQ ID NO 1
<211> LENGTH: 484
<212> TYPE: DNA
<213> ORGANISM: Artificial sequence
<220> FEATURE:
<223> OTHER INFORMATION: Mutant of codifying region for protein E3-19K
      of human adenovirus serotype 5

<400> SEQUENCE: 1
atgattaggt acataatcct aggtttactc acccttgcgt cagcccacgg taccacccaa      60
aaggtggatt ttaaggagcc agcctgtaat gttacattcg cagctgaagc taatgagtgc     120
accactctta taaatgcac acagaacat gaaaagctgc ttattcgcca caaaaacaaa       180
attggcaagt atgctgttta tgctatttgg cagccaggtg acactacaga gtataatgtt     240
acagttttcc agggtaaaag tcataaaact tttatgtata cttttccatt ttatgaaatg     300
tgcgacatta ccatgtacat gagcaaacag tataagttgt ggccccccaca aaattgtgtg    360 gaaaacactg gcactttctg ctgcactgct atgctaatta cagtgctcgc tttggtctgt    420
accctactct atattaaata caaaaagcag acgcagcttt attgaggaaa agaaaatgcc    480
ttaa                                                                   484

<210> SEQ ID NO 2
<211> LENGTH: 7
<212> TYPE: PRT
<213> ORGANISM: Artificial sequence
<220> FEATURE:
<223> OTHER INFORMATION: Fragment of mutated carboxy-terminal fragment
      of protein E3-19K of human adenovirus type 5

<400> SEQUENCE: 2

Lys Lys Gln Thr Gln Leu Tyr
1               5

<210> SEQ ID NO 3
<211> LENGTH: 13
<212> TYPE: PRT
<213> ORGANISM: Human adenovirus type 5

<400> SEQUENCE: 3

Lys Ser Arg Arg Ser Phe Ile Glu Glu Lys Lys Met Pro
1               5                   10

<210> SEQ ID NO 4
<211> LENGTH: 483
<212> TYPE: DNA
<213> ORGANISM: Artificial sequence
<220> FEATURE:
<223> OTHER INFORMATION: Mutant of codifying region for protein E3-19K
      of human adenovirus type 5

<400> SEQUENCE: 4
atgattaggt acataatcct aggtttactc acccttgcgt cagcccacgg taccacccaa      60
aaggtggatt ttaaggagcc agcctgtaat gttacattcg cagctgaagc taatgagtgc     120
accactctta taaatgcac acagaacat gaaaagctgc ttattcgcca caaaaacaaa       180
attggcaagt atgctgttta tgctatttgg cagccaggtg acactacaga gtataatgtt     240
acagttttcc agggtaaaag tcataaaact tttatgtata cttttccatt ttatgaaatg     300
tgcgacatta ccatgtacat gagcaaacag tataagttgt ggccccccaca aaattgtgtg    360 gaaaacactg gcactttctg ctgcactgct atgctaatta cagtgctcgc tttggtctgt    420
accctactct atattaaata caaaagcaga cgcagcttta ttgaggaaag cagcatgcct    480
taa                                                                   483

```
<210> SEQ ID NO 5
<211> LENGTH: 13
<212> TYPE: PRT
<213> ORGANISM: Artificial sequence
<220> FEATURE:
<223> OTHER INFORMATION: Fragment of mutated carboxy-terminal fragment
      of protein E3-19K of human adenovirus type 5

<400> SEQUENCE: 5

Lys Ser Arg Arg Ser Phe Ile Glu Glu Ser Ser Met Pro
1               5                   10

<210> SEQ ID NO 6
<211> LENGTH: 5
<212> TYPE: PRT
<213> ORGANISM: Human adenovirus type 5

<400> SEQUENCE: 6

Glu Lys Lys Met Pro
1               5

<210> SEQ ID NO 7
<211> LENGTH: 2512
<212> TYPE: DNA
<213> ORGANISM: Artificial sequence
<220> FEATURE:
<223> OTHER INFORMATION: Sequence with the regulatory regions DM1
      insulator (from position 367 to 1095); a fragment of the E2F1
      promoter (from position 1282 to 1545); the ccacc kozak sequence
      (from position 1546 to 1550); and the E1a- 24 gene (from position
      1551 to 2512).

<400> SEQUENCE: 7
catcatcaat tataccttcc attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg     180 gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tctctagcat cgatgtcgag     360
gatccctcga gaccctgaaa ctgtcttcga ctccggggcc ccgttggaag actgagtgcc     420
cggggcacgg cacagaagcc gcgcccaccg cctgccagtt cacaaccgct ccgagcgtgg     480
gtctccgccc agctccagtc ctgtgatccg ggcccgcccc ctagcggccg gggagggagg     540
ggccgggtcc gcggccggcg aacgggggctc gaagggtcct tgtagccggg aatgctgctg     600
ctgctgctgg ggggatcaca gaccatttct ttctttcggc caggctgagg ccctgacgtg     660
gatgggcaaa ctgcaggcct gggaaggcag caagccgggc cgtccgtgtt ccatcctcca     720
cgcaccccca cctatcgttg gttcgcaaag tgcaaagctt tcttgtgcat gacgccctgc     780
tctggggagc gtctggcgcg atctctgcct gcttactcgg gaaatttgct tttgccaaac     840 ccgcttttc ggggatcccg cgcccccctc ctcacttgcg ctgctctcgg agccccagcc     900
ggctccgccc gcttcggcgg tttggatatt tattgacctc gtcctccgac tcgctgacag     960
gctacaggac cccaacaac cccaatccac gttttggatg cactgagacc ccgacattcc     1020
tcggtattta ttgtctgtcc ccacctagga ccccacccc cgaccctcgc gaataaaagg     1080
ccctccatct gccctcgag tctagagatg gccgcaataa aatatcttta ttttcattac     1140
atctgtgtgt tggttttttg tgtgaatcga tagtactaac atacgctctc atcaaaaca      1200 aaacgaaaca aaacaaacta gcaaaatagg ctgtccccag tgcaagtgca ggtgccagaa     1260
```

-continued

```
catttctcta tcgataggta ccatccggac aaagcctgcg cgcgccccgc cccgccattg      1320
gccgtaccgc cccgcgccgc cgccccatct cgccctcgc cgccgggtcc ggcgcgttaa      1380
agccaatagg aaccgccgcc gttgttcccg tcacggccgg ggcagccaat tgtggcggcg      1440
ctcggcggct cgtggctctt tcgcggcaaa aaggatttgg cgcgtaaaag tggccgggac      1500
tttgcaggca gcggcggccg ggggcggagc gggatcgagc cctcgccacc atgagacata      1560
ttatctgcca cggaggtgtt attaccgaag aaatggccgc cagtcttttg gaccagctga      1620
tcgaagaggt actggctgat aatcttccac ctcctagcca ttttgaacca cctacccttc      1680
acgaactgta tgatttagac gtgacggccc ccgaagatcc caacgaggag gcggtttcgc      1740
agatttttcc cgactctgta atgttggcgg tgcaggaagg gattgactta ctcacttttc      1800
cgccggcgcc cggttctccg gagccgcctc accttccccg gcagcccgag cagccggagc      1860
agagagcctt gggtccggtt tctatgccaa accttgtacc ggaggtgatc gatccaccca      1920
gtgacgacga ggatgaagag ggtgaggagt ttgtgttaga ttatgtggag caccccgggc      1980
acggttgcag gtcttgtcat tatcaccgga ggaatacggg ggacccagat attatgtgtt      2040
cgctttgcta tatgaggacc tgtggcatgt ttgtctacag taagtgaaaa ttatgggcag      2100
tgggtgatag agtggtgggt ttggtgtggt aattttttttt ttaattttta cagttttgtg      2160
gtttaaagaa ttttgtattg tgattttttt aaaaggtcct gtgtctgaac ctgagcctga      2220
gcccgagcca gaaccggagc ctgcaagacc tacccgccgt cctaaaatgg cgcctgctat      2280
cctgagacgc ccgacatcac ctgtgtctag agaatgcaat agtagtacgg atagctgtga      2340
ctccggtcct tctaacacac ctcctgagat acacccggtg gtcccgctgt gccccattaa      2400
accagttgcc gtgagagttg gtgggcgtcg ccaggctgtg gaatgtatcg aggacttgct      2460
taacgagcct gggcaacctt tggacttgag ctgtaaacgc cccaggccat aa            2512
```

<210> SEQ ID NO 8
<211> LENGTH: 1773
<212> TYPE: DNA
<213> ORGANISM: Artificial sequence
<220> FEATURE:
<223> OTHER INFORMATION: Sequence codifying the fiber of the human adenovirus type 5 (from position 1 to 1638; and position 1666 to 1773) containing an insertion of the peptide RGD (from position 1639 to 1665) containing the RGD motif (from 1648 to 1656).

<400> SEQUENCE: 8

```
atgaagcgcg caagaccgtc tgaagatacc ttcaaccccg tgtatccata tgacacggaa        60
accggtcctc caactgtgcc tttcttact cctcccttg tatcccccaa tgggtttcaa       120
gagagtcccc ctggggtact ctctttgcgc ctatccgaac ctctagttac ctccaatggc       180
atgcttgcgc tcaaaatggg caacggcctc tctctggacg aggccggcaa ccttacctcc       240
caaaatgtaa ccactgtgag cccacctctc aaaaaaacca agtcaaacat aaacctggaa       300
atatctgcac ccctcacagt tacctcagaa gccctaactg tggctgccgc cgcacctcta       360
atggtcgcgg gcaacacact caccatgcaa tcacaggccc cgctaaccgt gcacgactcc       420
aaacttagca ttgccaccca aggacccctc acagtgtcag aaggaaagct agccctgcaa       480
acatcaggcc ccctcaccac caccgatagc agtaccctta ctatcactgc ctcaccccct       540
ctaactactg ccactggtag cttgggcatt gacttgaaag agcccattta tacacaaaat       600
ggaaaactag gactaaagta cggggctcct ttgcatgtaa cagacgacct aaacactttg       660
accgtagcaa ctggtccagg tgtgactatt aataatactt ccttgcaaac taaagttact       720
```

```
ggagccttgg gttttgattc acaaggcaat atgcaactta atgtagcagg aggactaagg      780
attgattctc aaaacagacg ccttatactt gatgttagtt atccgtttga tgctcaaaac      840
caactaaatc taagactagg acagggccct cttttttataa actcagccca caacttggat     900
attaactaca acaaaggcct ttacttgttt acagcttcaa acaattccaa aaagcttgag      960
gttaacctaa gcactgccaa ggggttgatg tttgacgcta cagccatagc cattaatgca     1020
ggagatgggc ttgaatttgg ttcacctaat gcaccaaaca caaatcccct caaaacaaaa     1080
attggccatg gcctagaatt tgattcaaac aaggctatgg ttcctaaact aggaactggc     1140
cttagttttg acagcacagg tgccattaca gtaggaaaca aaaataatga taagctaact     1200
ttgtggacca caccagctcc atctcctaac tgtagactaa atgcagagaa agatgctaaa     1260
ctcactttgg tcttaacaaa atgtggcagt caaatacttg ctacagtttc agttttggct     1320
gttaaaggca gtttggctcc aatatctgga acagttcaaa gtgctcatct tattataaga     1380
tttgacgaaa atggagtgct actaaacaat tccttcctgg acccagaata ttggaacttt     1440
agaaatggag atcttactga aggcacagcc tatacaaacg ctgttggatt tatgcctaac     1500
ctatcagctt atccaaaatc tcacggtaaa actgccaaaa gtaacattgt cagtcaagtt     1560
tacttaaacg gagacaaaac taaacctgta acactaacga tcacactaaa cggtacacag     1620
gaaacaggag acacaacttg tgactgccgc ggagactgtt tctgcccatc tgcatactct     1680
atgtcatttt catgggactg gtctggccac aactacatta atgaaatatt tgccacatcc     1740
tcttacactt tttcatacat tgcccaagaa taa                                  1773
```

US 8,974,777 B2

ADENOVIRUS WITH MUTATIONS IN THE ENDOPLASMIC RETICULUM RETENTION DOMAIN OF THE E3-19K PROTEIN AND THEIR USE IN CANCER TREATMENT

PRIORITY INFORMATION

This application is a continuation of PCT application no. PCT/EP2008/052960 designating the United States and filed Mar. 12, 2008; which claims the benefit of the filing date of European patent application no. EP 200700665 filed Mar. 14, 2007; both of which are hereby incorporated herein by reference in their entireties.

FIELD OF THE INVENTION

The field of the invention relates generally to the treatment of cancer and more particularly to adenoviruses which contain the E3-19K gene mutated in its endoplasmic reticulum retention domain and the use of these adenoviruses to treat cancer.

BACKGROUND OF THE INVENTION

Current cancer treatment is based mainly on chemotherapy, radiotherapy and surgery. Despite a high rate of success when the treatment is applied at early stages, most cases of advanced disease are not curable because tumors cannot be excised by surgery or radio and chemotherapy doses that can be administered are limited by toxicity to normal cells. To alleviate this problem biotechnology strategies that seek higher selectivity and potency have been developed. Among them, gene therapy and virotherapy use viruses with a therapeutic aim against cancer. In gene therapy the virus is modified to avoid its replication and to function as a vehicle or vector of therapeutic genetic material. Conversely, virotherapy uses viruses that replicate and propagate selectively in tumor cells. In virotherapy the tumor cell dies by the cytopathic effect caused by the replication of the virus inside the cell rather than by the effect of a therapeutic gene. The preferential replication in a tumor cell is known as oncolysis. Viruses that replicate selectively in tumors are known as oncolytic viruses.

Cancer virotherapy is older than gene therapy. First reports on cancer cures with viruses date to the beginning of the past century. In 1912 De Pace obtained tumor regressions after the inoculation of rabies virus in cervical carcinomas (De Pace N. Sulla scomparsa di un enorme cranco vegetante del collo dell'utero senza cura chirurgica. Ginecologia 1912; 9:82-89). Since then, many types of viruses have been injected in tumors to treat them. There are viruses that present a natural oncotropism such as autonomous parvovirus, vesicular stomatitis virus and reovirus. Other viruses can be genetically manipulated to achieve selective replication in tumors. For example, Herpes Simplex virus (HSV) has been rendered oncotropic by deleting the ribonucleotide reductase gene, an enzymatic activity not necessary in cells ongoing active proliferation such as tumor cells. However, adenovirus, due to its low pathogenicity and high efficacy to infect tumor cells has been the most commonly used virus in virothrapy and gene therapy of cancer.

Fifty one serotypes of adenovirus have been identified and grouped in six differentiated groups, A to F.

The human adenovirus type 5 (Ad5), which belongs to group C, consists of an icosahedral protein capsid which contains a linear DNA of 36 kilobases. In adults, Ad5 infection is often asymptomatic and causes colds and conjunctivitis in children. In general terms, Ad5 infects epithelial cells, which in a natural infection are the bronchial epithelial cells. It enters the cell by means of the interaction of the fiber, a virus protein that extends as an antenna from the twelve vertexes of the capsid, with a cellular protein involved in intercellular adhesion known as Coxsackie-Adenovirus Receptor (CAR). When the virus DNA reaches the nucleus, the transcription of early genes (E1 to E4) begins. The first genes to be expressed are those from the early 1A region (E1A). E1A binds to cellular protein pRb (retinoblastoma protein) to release the transcription factor E2F to activate the transcription of other virus genes such as E2, E3, and E4, and of cellular genes that activate the cell cycle. On the other hand, E1B binds to the transcription factor p53 to activate the cell cycle and to inhibit the apoptosis of the infected cell. E2 encodes proteins for replication of the virus. E3 encodes proteins that inhibit the antiviral immune response. E4 encodes proteins to transport virus ARN. The expression of early genes leads to the replication of the genome and, once replicated, to the activation of the major late promoter. This promoter drives the expression of an mRNA that is processed by differential splicing to give all the RNAs that encode the structural proteins that form the capsid.

As particularly relevant to the present invention, E3 proteins are described with more detail. At the early phase of the virus life cycle, before replication of the genome, E3 genes are expressed from the E3 promoter. This promoter drives the expression of a pre-mRNA which generates nine different mRNAs by splicing. In most of the serotypes of the adenovirus, namely those of the groups B, C, D and E, seven proteins (polypeptides) are synthesized from these mRNAs: E3-12.5K, E3-6.7K, E3-19K, E3-11.6K (also known as adenovirus death protein or ADP), E3-10.4K (RIDalpha), E3-14.5K (RIDbeta), and E3-14.7K (from left to right position in the genome). At the late phase the E3 promoter is repressed and the major late promoter is activated. From this promoter one pre-mRNA is synthesized which gives different mRNAs by splicing. The only E3 protein synthesized from these late mRNAs is E3-11.6K (ADP). ADP or E3-11.6K is an integral membrane protein located at the nuclear, golgi and endoplasmic reticulum membranes. It plays a role in the lysis of the infected cell. The remaining E3 proteins have functions related with the inhibition of the immune response against the infected cell. For example, E3-6.7K, RIDalpha, RIDbeta and E3-14.7K protect the cell from TNF-mediated apoptosis. E3-19K is a membrane protein that retains the major histocompatibility class 1 proteins (MHC-I) at the endoplasmic reticulum. Hence E3-19K avoids antigen presentation in the membrane of the infected cells. There are two key peptidic regions or domains to mediate this E3-19K function. One is the E3-19K MHC-I binding domain. The other one is a peptidic sequence at the carboxy-terminus end of E3-19K that retains the protein in the endoplasmic reticulum and avoids its transit to the cellular membrane. The description of these functional domains of E3-19K with mutations specific to these domains has been performed using E3-19K isolated in expression plasmids (Gabathuler R, Kvist S. The endoplasmic reticulum retention signal of the E3/19K protein of adenovirus type 2 consists of three separate amino acid segments at the carboxy terminus. J Cell Biol 1990; 111 (5 Pt 1):1803-10).

There are two important points to consider regarding the design of oncolytic adenoviruses: selectivity and potency. To achieve selectivity towards a tumor cell two strategies have been used: the deletion of virus functions that are not necessary in tumor cells and the substitution of viral promoters with tumor selective promoters. With such genetic modifications, a considerable level of selectivity has been obtained, with a replication efficiency in a tumor cell 10000-fold higher than in a normal cell. With regard to oncolytic potency several genetic modifications to increase it have been described as well. These modifications affect either the entry of the virus in the cell or the release of virus from the cell. To increase the entry step, the capsid proteins that the virus uses to infect the cell have been modified. For example, the insertion of the RGD peptide (Arginine-Glycine-Asparagine motif) in the fiber allows adenovirus to use integrins to dock in the cell and not only to internalize as it is the case with wild type adenovirus. The use of integrins as cellular receptors of the virus increases the infectivity and the oncolytic potency. Regarding the modifications that increase the release of virus from the infected cell, two have been described: the deletion of E1B-19K and the overexpression of E3-11.6K (ADP). E1B-19K is an apoptosis inhibitor homolog to Bcl-2. E1B-19K deletion increases cell death by premature apoptosis of the infected cell. This premature apoptosis often results in a lower total virus production in many infected cell lines, however it accelerates the fast release of virus and, in turn, the spread of virus in a cell culture. Accordingly the mutants that do not express E1B-19K present a large plaque phenotype compared to the wild type adenovirus in a plaque assay. Another strategy used to increase the oncolytic potency of adenovirus is the overexpression of E3-11.6K (ADP) protein. This protein plays a role in the lysis of the infected cell and ADP overexpression increases the release of the virus accumulated inside the nucleus. The phenotype of ADP-overexpressing viruses is also characterized by large plaques and the presence of more viruses in the supernatant of infected cells. ADP overexpression has been achieved by two mechanisms: 1) Eliminating the other E3 genes except ADP, or except ADP and E3-12.5K. This deletion removes other splicing sites in the pre-mRNA driven by the E3 promoter. Without the competition for these splice sites, the processing of the mRNA encoding ADP is favored. 2) Inserting the ADP gene after an strong promoter.

The present invention discloses a novel and improved mechanism to increase the release of adenovirus from the infected cell based on a mutation of E3-19K protein.

SUMMARY OF THE INVENTION

Specifically, this invention describes an enhancement of adenovirus release based on the mutation of the endoplasmic reticulum retention domain of E3-19K protein. This invention demonstrates that the phenotype associated to the mutation that affects the cellular localization of E3-19K is not associated to the over-expression of ADP and therefore it is a different mechanism neither previously described nor suggested to increase the release of adenovirus out of the infected cell.

A random mutagenesis of the adenovirus 5 genome followed by a selection of mutants that have acquired higher oncolytic potency was made. The mutagenesis with sodium nitrite generates transitional mutations where a nucleotide base deamination is produced. After the replication of DNA, these deaminated bases generate new pairings and the mutations are fixed. After the mutagenesis of an adenovirus 5 stock the resulting pool was amplified in a cancer cell line and purified with standard procedures. The virus stock corresponds to the Adenovirus Reference Material (ARM) (GenBank sequence file AY339568). The bioselection process of oncolytic mutants was performed in vivo in immunodeficient mice (nude mice) with previously inoculated human tumors. Viruses that persisted longer in blood and that replicated more efficiently in tumors were isolated, amplified and injected again in tumor-bearing mice in subsequent rounds of bioselection. There is an existing example of the use of this random method to discover mutants that present a higher oncolytic potency although the bioselection process used in this precedent is different (Yan W, Kitzes G, Dormishian F, Hawkins L, Sampson-Johannes A, Watanabe J, et al. Developing novel oncolytic adenoviruses through bioselection. J Virol 2003; 77(4):2640-50). This precedent discovers other mutations different to the one subject of the present invention.

The present invention relates to an adenovirus characterized by containing a mutation in the endoplasmic reticulum retention domain of E3-19K. In particular, the carboxy-terminal domain of E3-19K is eliminated or modified to prevent the retention of E3-19K in the endoplasmic reticulum and to cause its transit to the plasma membrane. An adenovirus that replicates and that contains this particular mutation of E3-19K is released more efficiently from the infected cell. This higher release causes a higher oncolytic effect. This enhanced oncolytic effect is useful to treat cancer.

The identification that the mutation of the carboxy-terminus end of E3-19K increases the release of adenovirus from the infected cell is surprising because the described function of E3-19K is an immunomodulatory function. In particular, a function described for E3-19K relates to the binding to MHC-I and to the retention of MHC-I in the endoplasmic reticulum to avoid the transit of MHC-I to the plasma membrane and the presentation of antigens associated to MHC-I. In consequence, the phenotype of adenovirus mutants that do not express E3-19K is characterized by the presence of MHC-I at the plasma membrane and by a higher immune response against the virus. This phenotype does not affect the propagation of adenovirus in cell cultures in vitro and, therefore the experts in the field of adenoviruses as gene therapy vectors have commonly deleted the entire E3 region with no adverse effects on virus production. Besides this knowledge on the phenotype of adenoviruses that do not express E3-19K, the phenotype that characterizes the adenoviruses with partial deletions of E3-19K is not known because the functional study of E3-19K domains has been performed with the E3-19K protein isolated, out of the context of the adenovirus (Gabathuler R, Kvist S. The endoplasmic reticulum retention signal of the E3/19K protein of adenovirus type 2 consists of three separate amino acid segments at the carboxy terminus. J Cell Biol 1990; 111(5 Pt 1):1803-10). These studies have never suggested that the deletion of the carboxy-terminus tail or the endoplasmic reticulum retention domain of E3-19K could increase virus release. Thus, there is no rational previous knowledge that suggests that the modification of the endoplasmic reticulum retention domain of E3-19K may result in a higher release of adenovirus from the infected cell. This result arises from the screening of a library of random mutants of adenovirus, performed in the present invention, using procedures that favour the selection of adenoviruses that are released more efficiently from infected cells.

Thus the present invention encompasses an adenovirus wherein this adenovirus is replicative and contains a mutation in the endoplasmic reticulum retention domain of E3-19K.

The E3-19K mutation considered in this invention can be an insertion, change or deletion of one or more base pairs of the gene sequence that encodes E3-19K. In all cases the effect is the same: it produces a change in the endoplasmic reticulum retention domain of E3-19K that results in E3-19K relocation from the endoplasmic membrane to the plasma membrane. In the same manner, other mutations that indirectly result in the same relocation of E3-19K are object of the present invention. For example, the insertion of protease target sites that remove the carboxy-terminus of E3-19K, or the insertion of alternative intracellular trafficking signals that can relocate E3-19K to the plasma membrane.

In another embodiment of the invention, the replicative adenovirus which contains a mutation in the endoplasmic reticulum retention domain of E3-19K is also mutated in one or more genes of the group E1a, E1b, E4, and VA-RNAs to achieve selective replication in tumors.

Another embodiment of the present invention is a replicative adenovirus which comprises a mutation in the endoplasmic reticulum retention domain of E3-19K and which further comprises a tissue-specific promoter or a tumor-specific promoter to achieve selective replication in tumors.

In another embodiment of the present invention, the replicative adenovirus comprises a mutation in the endoplasmic reticulum retention domain of E3-19K and further comprises promoter sequences to control the expression of one or more genes from the group consisting of E1a, E1b, E2, and E4, to achieve selective replication in tumors.

Another embodiment of the present invention is a replicative adenovirus which comprises a mutation in the endoplasmic reticulum retention domain of E3-19K and capsid modifications to increase its infectivity or targeting to a receptor present in a tumor cell.

Another object of the invention is a replicative adenovirus comprising a mutation in the endoplasmic reticulum retention domain of E3-19K and further comprising genes commonly used in the field of cancer gene therapy. Preferably, the genes commonly used in the field of cancer gene therapy are selected from the group consisting of prodrug-activating genes, tumor-supressor genes and immunostimulatory genes.

Another embodiment of the present invention is a replicative adenovirus which comprises a mutation in the endoplasmic reticulum retention domain of E3-19K and genome modifications that result in an enhancement of the expression of said E3-19K protein.

The replicative adenovirus of the present invention which comprises the nucleotide sequence SEQ ID NO: 1.

In another aspect of the invention, the replicative adenovirus expresses an endoplasmic reticulum retention domain of E3-19K with a carboxy-terminus tail having a SEQ ID NO: 2.

Another object of the present invention is a replicative adenovirus which comprises a mutation in the endoplasmic reticulum retention domain of E3-19K and wherein said adenovirus comprises the nucleotide sequence SEQ ID NO 4.

The replicative adenovirus of the invention expresses an endoplasmic reticulum retention domain of E3-19K with a carboxy-terminus tail having a SEQ ID NO 5.

Another object of the invention is a replicative adenovirus comprising a mutation in the endoplasmic reticulum retention domain of E3-19K, and wherein said adenovirus comprises at least the nucleotide sequences SEQ ID NO:1, SEQ ID NO: 7 and SEQ ID NO: 8.

The replicative adenovirus of the present invention expresses an endoplasmic reticulum retention domain of E3-19K with a carboxy-terminus tail having a SEQ ID NO: 2; and containing the insertion of the RGD motif (defined from position 1648 to 1656 of SEQ ID NO:8); and regulatory regions conferring selective replication of said adenovirus in tumor cells, said regulatory regions consisting in DM1 insulator (defined from position 367 to 1095 of SEQ ID NO: 7), a fragment of the E2F1 promoter (defined from position 1282 to 1545 of SEQ ID NO: 7), the ccacc kozak sequence (defined from position 1546 to 1550 of SEQ ID NO: 7) and the E1a-Δ24 mutated adenovirus gene (defined from position 1551 to 2512 of SEQ ID NO:7).

Another object of the present invention is a pharmaceutical composition comprising a pharmacologically effective dosage of a replicative adenovirus comprising a mutation in the endoplasmic reticulum retention domain of E3-19K and one or more pharmaceutically acceptable carriers or excipients.

Another object of the invention is a replicative adenovirus as defined above for use as a medicament.

The replicative adenovirus of the invention as a prophylactic and/or therapeutic agent in cancer.

The present invention also provides a novel method to treat cancer comprising the administration of a replicative adenovirus which contains a mutation in the endoplasmic reticulum retention domain of E3-19K.

Another object of the invention is the use of the replicative adenovirus as defined above in the preparation of a pharmaceutical formulation for the treatment or prevention of cancer or the pre-malignant disease leading to cancer.

In another embodiment, the E3-19K mutant adenovirus of the invention may be used in combination with other cancer therapies such as chemotherapy or radiotherapy.

The present invention describes a replicative adenovirus which contains a mutation in the endoplasmic reticulum retention domain of E3-19K and the use of said adenovirus for the treatment or prevention of cancer or a pre-malignant disease leading to cancer. There are previous reports on the overexpression of E3-11.6K (ADP) or the deletion of E1B-19K in oncolytic adenoviruses. Contrary to the present invention, these modifications previously described neither imply nor require the localization of E3-19K at the plasma membrane and their mechanism of action is different. Previous to the present invention, the activity of an E3-19K protein unable to remain docked at the endoplasmic reticulum never has been analysed in a virus genome. The activity of said protein in relation to the increase of oncolytic potency associated with the release of virus is surprising because the only function described for E3-19K is that of binding MHC-I and, through this binding E3-19K decreases the presentation of antigens and the immune response.

The adenoviruses that contain a mutation in the endoplasmic reticulum retention domain of E3-19K object of the present invention are propagated and amplified in cell lines commonly used in the field of gene therapy and virotherapy, such as HEK-293 and A549. The procedures to purify an adenovirus which contains a mutation in the endoplasmic reticulum retention domain of E3-19K for its use in the treatment of cancer are the same procedures as those described for other adenoviruses and adenovirus vectors used in virotehrapy and gene therapy of cancer.

The invention addresses the need for improved therapies for cancer including, but not limited to, pancreatic cancer, colon cancer and lung cancer. The treatment of cancer with an oncolytic adenovirus which contains a mutation in the endoplasmic reticulum retention domain of E3-19K can be performed by direct injection of the virus inside the tumor or by systemic administration in cancer patients using standard methods in the fields of gene therapy and virotherapy with adenoviruses.

BRIEF DESCRIPTION OF THE DRAWINGS

The appended drawings have been included herein so that the above features, advantages and constructs will become clear and can be understood in detail. These drawings form part of the specification and illustrate preferred embodiments but should not be considered to limit the scope of the invention.

FIG. 4. Sequence of the mutation present in AdT1 (SEQ ID NO: 1) compared with the sequence of wild type adenovirus serotype 5 (Adwt). The Adwt nucleotide sequence represented corresponds to the fragment of AY339865 coding for the carboxy-terminus tail of E3-19K (SEQ ID NO: 3). AdT1 virus was isolated form a random library of adenovirus mutants by a selection in vivo (in immunodeficient mice with xenografted human tumors) for a longer persistence in blood and in tumors after intravenous administration. The AdT1 virus contains an insertion of an adenosine nucleotide (A) at the position 445 of the DNA encoding the protein E3-19K. This mutation (hereto follows named 445-A) changes the sequence of amino acids and eliminates the endoplasmic reticulum retention domain of E3-19K. Compared to the wild type sequence, the mutated sequence yields a shorter carboxy-terminus tail.

DETAILED DESCRIPTION OF THE INVENTION

Figure 1:
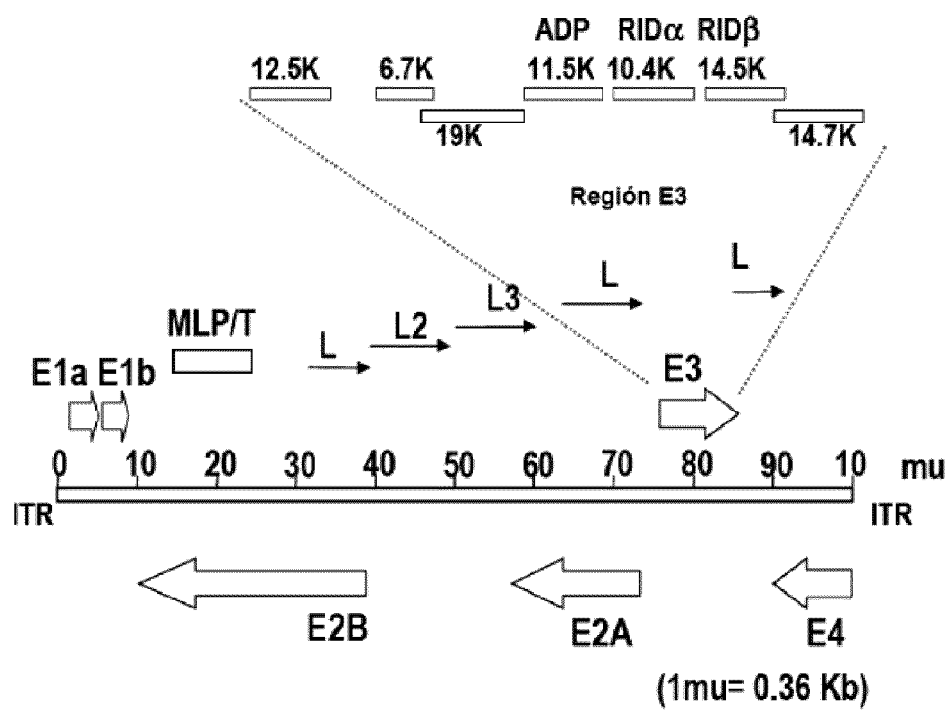
FIG. 1. Schematic representation of the genome of human adenovirus serotype 5 (GenBank sequence file AY339865). Conventionally the linear genome of 35934 base pairs is divided in 100 map units (mu) from left to right. The regions encoding early (E1a E4) and late (L) RNAs are indicated. The E3 region encodes seven proteins derived from a pre-mRNA transcript by differential splicing. The invention relates to the E3-19K protein and mutations that affect its carboxy-terminus tail.

A. Structure and Function of Adenoviruses with Mutations in the Endoplasmic Reticulum Retention Domain of E3-19K and Their Use in Cancer Treatment.

The present invention describes the use of adenoviruses with mutations in the endoplasmic reticulum retention domain of E3-19K for the treatment of cancer. The treatment is based on the replication of these viruses in tumors.

Several methods are used to manipulate the viral genome. The methods used for the construction of genetically modified adenovirus are well established in the field of gene therapy and adenovirus virotherapy. The most commonly used method is based on the introduction of the desired genetic modification into a plasmid containing the region of the adenovirus genome to be modified, and then performing homologous recombination in bacteria with a plasmid containing the rest of the viral genome.

Various types of mutations and genetic manipulations have been carried out to obtain tumor selective replication. One of these is the insertion of promoters which are active in tumor cells and are used to control the expression of viral genes. These promoters include the E2F promoter, the telomerase (hTERT) promoter, the tyrosinase promoter, the prostate specific antigene (PSA) promoter, the alpha-fetoprotein promoter, the cyclooxigenase 2 (cox-2) promoter and artificial promoters based on the introduction of transcription factor binding sites such as HIF-1 (Hypoxia-inducible factor), Ets (transcription factors of the E26 family) and tcf (T-cell factor). One embodiment of the present invention is the use of adenoviruses with mutations in the endoplasmic reticulum retention domain of E3-19K in combination with these promoters.

Another modification described to achieve tumor-selective replication is the deletion of early E1A functions which block the pRB pathway. The selective replication of such mutants has been demonstrated in several prior art documents. Other viral genes which interact directly with pRB such as E4 and E4orf6/7 are candidates to be deleted in order to achieve selective replication in tumor cells. One embodiment of the invention is the use of adenoviruses with mutations in the endoplasmic reticulum retention domain of E3-19K in combination with these E1 deleted mutants which confer selective replication.

Another modification described to achieve tumor-selective replication is the deletion of adenovirus genes coding for the virus-associated RNAs (VA-RNAs). These RNAs block the antiviral activity of interferon and their deletion results in adenoviruses that are sensible to interferon inhibition. Due to the characteristic truncation in the interferon pathway in tumor cells such adenoviruses replicate normally in tumors. One embodiment of the present invention is the use of adenoviruses with mutations in the endoplasmic reticulum retention domain of E3-19K in combination with these deletions in the virus-associated RNAs which confer selective replication.

In another embodiment of this invention, adenoviruses with mutations in the endoplasmic reticulum retention domain of E3-19K can contain modifications in their capsid to increase their infectivity or direct themselves to receptors present in the tumor cell. The adenoviral capsid proteins have been genetically modified to include ligands which enhance the infectivity or direct the virus to a receptor present in the tumor cell. The direction of virus to the tumor can also be achieved with bifunctional ligands which bind to the virus in one end and to the tumor receptor in the other. To increase the blood persistence of adenovirus in order to increase the possibilities of reaching the disseminated tumor nodes, the capsid can also be coated with polymers like poly-ethyleneglycol. One embodiment of the present invention is the use of adenoviruses with mutations in the endoplasmic reticulum retention domain of E3-19K in combination with these capsid modifications.

Another embodiment of the present invention is an adenovirus which replicates (replicative adenovirus) and which contains a mutation in the endoplasmic reticulum retention domain of E3-19K and other genome modifications that result in an enhancement of the expression of said mutated E3-19K protein. There could be several ways to enhance the expression of the mutated E3-19K. For example, modifications of the E3 promoter to increase gene transcription or mutations that enhance the activity of virus proteins involved in processing virus RNAs and protein synthesis. As the mutated E3-19K provides a novel function, this overexpression would result in an increased function.

Another embodiment of the present invention refers to adenoviruses containing mutations in the endoplasmic reticulum retention domain of E3-19K which also contain other genes to increase their cytotoxicity in tumor cells, such as the thymidine kinase gene, the cytosine deaminase gene, pro-apoptotic genes, immunostimulating genes or tumor suppressor genes.

B. Production, Purification and Formulation of Adenoviruses with Mutations in the Endoplasmic Reticulum Retention Domain of E3-19K.

The adenoviruses described in this invention can be propagated following the standard methods in the field of adenovirology and adenoviral vectors, as disclosed in Graham F L, Prevec L. Manipulation of adenoviral vectors. Clifton, N.J.: Humana Press; 1991; and Alemany R, Zhang W. Oncolytic adenoviral vectors. Totowa, N.J.: Humana Press; 1999. The preferential method of propagation consists in the infection of a cell line that allows the replication of adenovirus with mutations in the endoplasmic reticulum retention domain of E3-19K. The lung adenocarcinoma A549 cell line is an example of such a cell line. The propagation is carried out, for example, as follows: A549 cells are grown in plastic cell culture plates and are infected with 50 viral particles per cell. Two days later the cytopathic effect evidences the viral production when cells detach forming 'grape-like' clusters. The cells are harvested and stored in tubes. The cells are centrifuged at 1000 g during 5 minutes and the cell pellet is frozen and thawed three times to free the intracellular virus. The resulting cell extract is centrifuged at 1000 g during 5 minutes and the supernatant containing the virus is layered onto a cesium chloride gradient and centrifuged for 1 hour at 35.000 g. The band of the virus obtained is collected and layered again onto another gradient of cesium chloride and centrifuged during 16 hours at 35.000 g. The band of virus is collected and dialyzed against PBS-10% glycerol. The dialyzed virus is aliquoted and kept at −80° C. The quantification of the number of viral particles and plaque forming units is done following standard protocols.

Phosphate buffered saline (PBS) with 10% glycerol is a standard formulation used for the storage of adenovirus. However, other formulations that improve the stability of the virus have been described.

C. Use of Adenoviruses with Mutations in the Endoplasmic Reticulum Retention Domain of E3-19K in Cancer Treatment.

This invention describes the use of adenoviruses with mutations in the endoplasmic reticulum retention domain of E3-19K for the treatment of cancer. The treatment is based on the replication of these viruses in tumor cells.

The protocols for the use of the viruses described in this invention for the treatment of cancer follow the same procedures as those used in the fields of virotherapy and gene therapy with adenovirus. There is broad experience in the use of replication-defective and replication-competent adenoviruses in the field of gene therapy. Several publications describe the treatment of tumor cells in vitro, in animal models or in clinical trials with patients. For the treatment of cells in vitro the purified adenovirus, in any of the formulations described above, is added to the culture medium to infect the tumor cells. To treat tumors in animal models or patients adenovirus can be delivered by local or regional administration through intratumoral or intracavital injection or systemically by intravenous injection. The treatment of tumors with the adenoviruses described within this invention can be used in combination with other therapeutic modalities like chemotherapy or radiotherapy, as previously described in the field of oncolytic adenovirus.

EXAMPLES

Example 1

An Adenovirus with a Mutation in the Endoplasmic Reticulum Retention Domain of E3-19K Spreads More Efficiently A library of mutagenized adenovirus was constructed as follows: $2 \times 10^{10}$ viral particles of human adenovirus type 5 (Adwt) were mutagenized by treatment with 0.7 M nitrous acid for 8 minutes. Then, the viral solution was diluted and dialyzed to eliminate the mutagenizing agent. In order to fix the mutations, the mutagenized virus was used to infect human tumor A549 cells and was amplified and purified with a cesium chloride gradient, as previously described. The mutagenized stock was injected into immunosuppressed mice with subcutaneous pancreatic NP-9 tumor xenografts. The virus contained in the blood of the mice 4 hours post-injection was amplified in vitro in A549 cells, purified, and injected again intravenously in subsequent rounds of bioselection. After several rounds, the virus contained in the tumor that had shown the best tumor regression (best oncolytic activity) was extracted (T1 extract). Finally, a virus named AdT1 was isolated from the T1 extract using a plaque assay.

Figure 2:
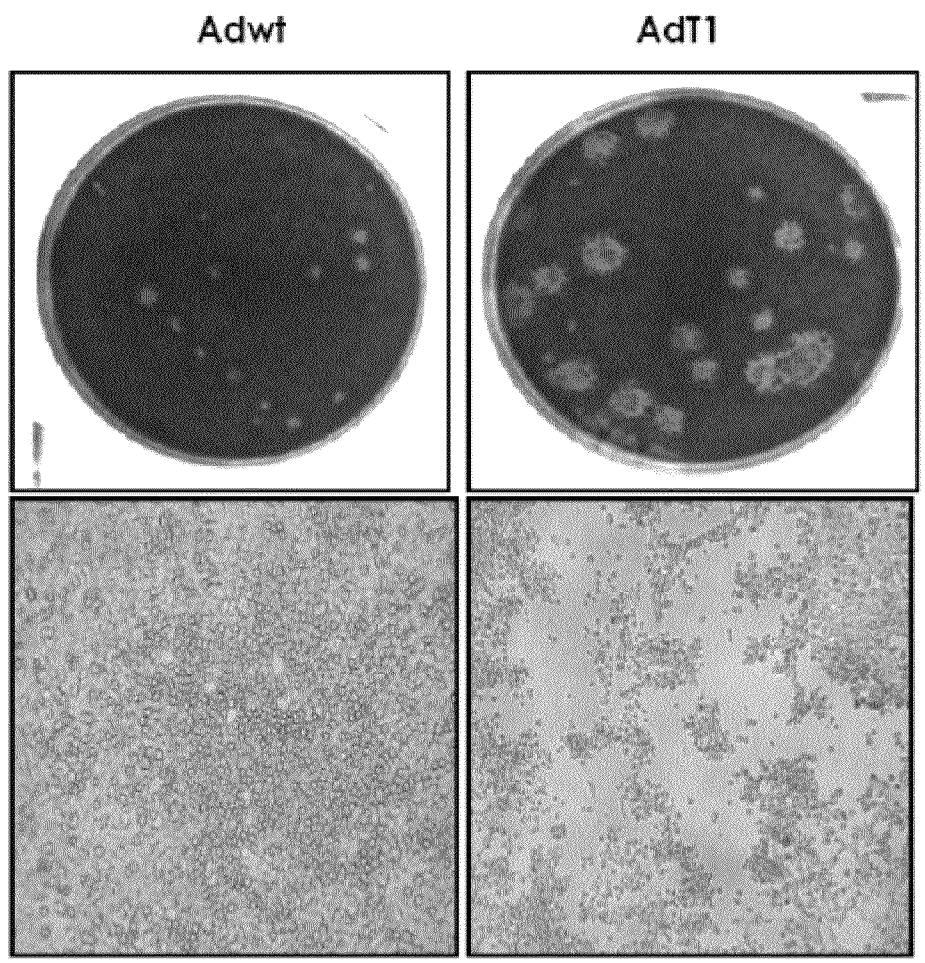
FIG. 2. Large plaque phenotype characteristic of the mutant AdT1. This mutant was obtained by random mutagenesis of the genome of human adenovirus type 5 (GenBank sequence file AY339865) followed by a screening based on the isolation of virus from blood and tumors of mice with implanted tumors. The cytotoxicity against tumor cells of the adenovirus AdT1 was compared with the cytotoxicity of wild type adenovirus (Adwt). Human tumor A549 cells were seeded in 6-well plates. At 80% confluence they were infected with serially diluted Adwt or AdT1. At 4 hours post-infection the virus was removed and the cell monolayer was covered by a layer of medium mixed with agarose. Infected cells were incubated during 6 days and then stained with neutral red, a dye absorbed only by living cells. The result shows that the plaques generated by AdT1 have a larger diameter than the plaques generated by Adwt (upper panels). The lower panels show a magnification of the plaques observed under the optical microscope (100×) where the higher cytotoxicity of the virus AdT1 can be noted.

This assay consists in the infection of a monolayer of tumor cells with a solution of diluted virus and the addition of an agarose overlay after infection. Agar forms a jellifying polymer which prevents the spread of the virus throughout the culture and causes the virus to spread focally from the initially infected cells resulting in the formation of more or less round areas without cells named plaques. A plaque assay demonstrated that the plaques of T1 were larger than the parental Ad5 plaques (see FIG. 2 of this invention). This phenotype indicated that AdT1's cell-to-cell spread was faster than Adwt. This enhanced spread is very interesting for its application in virotherapy of cancer, since it can increase the antitumor activity as demonstrated in this invention.

Figure 3:
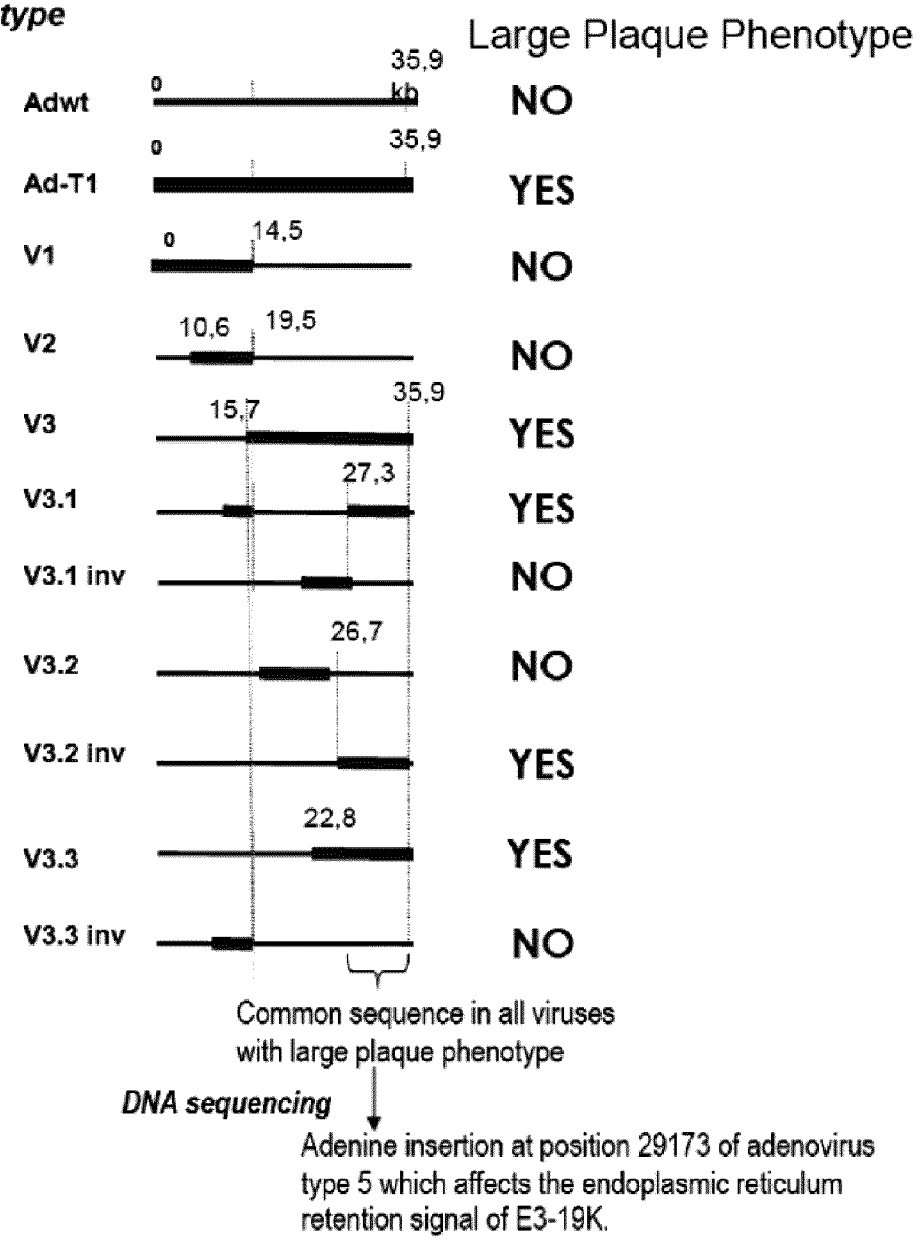
FIG. 3. Identification of the mutation that confers the large plaque phenotype to AdT1. A series of adenoviruses by recombination of Adwt and the mutant AdT1 were constructed and those recombinants presenting a large plaque phenotype were studied. In the figure Adwt genome is depicted as a fine line and AdT1 genome as a thick line. The common region present in all recombinants that showed a large plaque phenotype was sequenced. By comparison to the wild type adenovirus type 5 sequence we identified an insertion of one base pair (A in the sense strand from left to right of the virus genome) in the position 29173 of the adenovirus type 5. This insertion changes the endoplasmic reticulum retention signal of E3-19K.
Figure 5:
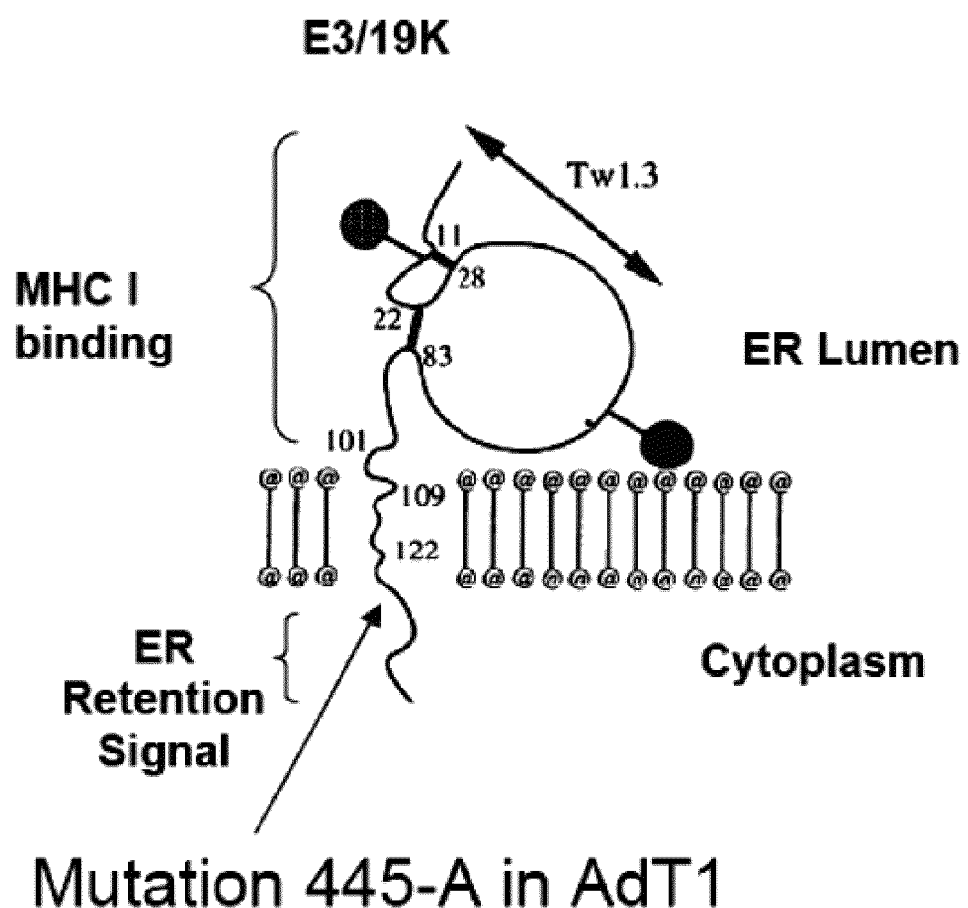
FIG. 5. Scheme of E3-19K protein and effect of the 445-A mutation in the endoplasmic reticulum retention domain of E3-19K. E3-19K is a transmembrane glycoprotein that docks at the endoplasmic reticulum of the adenovirus infected cells. Functionally, E3-19K contains a luminal domain (amino-terminus) which contains the amino acid residues that interact with the major histocompatibility complex class 1 proteins (MHC-1); and a cytoplasm domain (carboxy-terminus) that contains a positive signal for retention at the endoplasmic reticulum (EKKMP or SEQ ID NO: 6). The figure shows the epitope recognized by antibody Tw1.3, used for the detection of E3-19K. The mutation 445-A is a frame shift mutation at the C-terminus tail that removes the amino acid residues 156 to 160 corresponding to the EKKMP signal. This mutation results in a re-localization of E3-19K to the plasma membrane.

Once AdT1 virus was isolated the next step was the determination of the genetic modification responsible for the large-plaque phenotype. Several viruses were constructed by inserting fragments of the AdT1 genome into the Ad5 wild-type genome (see FIG. 3). This phenotypic map indicated that the mutation responsible for the large-plaque phenotype was present in a region from 75.8 (position 27300 of Ad5) to 100 map units of the adenovirus sequence. This region of AdT1 was sequenced and compared to the sequence of Adwt. The only mutation found was localized in the C-terminal region of the E3-19K protein in the endoplasmic reticulum retention domain (see FIGS. 4 and 5 of the invention). This mutation named 445-A inserts one base-pair (an adenine in the translational strand and the respective thymine in the complementary strand as can be seen in SEQ ID NO: 1) which changes the reading frame of the mRNA and results in a change in the residues 5'-KSRRSFIEEKKMP-3' of the C-terminal end of the native protein (SEQ ID NO: 3). To demonstrate that this mutation was responsible for the phenotype of virus AdT1 an adenovirus type 5 containing this mutation was constructed by site-directed mutagenesis. This virus named Ad-19K-445A gave the same large-plaque phenotype as virus AdT1, demonstrating the phenotype of AdT1 was caused by mutation E3-19K 445-A (see FIG. 6 of the invention).

Previous to this invention, the large-plaque phenotype indicative of a better cell-to-cell spread in cell cultures had never been associated to mutations in the endoplasmic reticulum retention domain of E3-19K. In fact, to the knowledge of the inventors, there are no publications of viruses containing mutations in this domain of E3-19K since the study of the domains of E3-19K has been performed with the cDNA of the isolated protein and not in the viral context, as above indicated. This previous study described that the mutation of the C-terminal tail of E3-19K results in the presence of the protein in the plasma membrane. In order to prove if the mutant E3-19K protein of AdT1 is localized to the plasma membrane, the E3-19K protein detection was performed with an antibody specific against this protein (Tw1.3 antibody) in cells that had not been permeabilized. In these conditions the cells infected with AdT1 presented cell surface expression of E3-19K while cells infected with Adwt did not (see FIG. 7 of the invention). When permeabilizing the membranes, the fraction of E3-19K in the endoplasmic reticulum becomes accessible to the antibody and is detected in both the cells infected with AdT1 and with Adwt.

Figure 6:
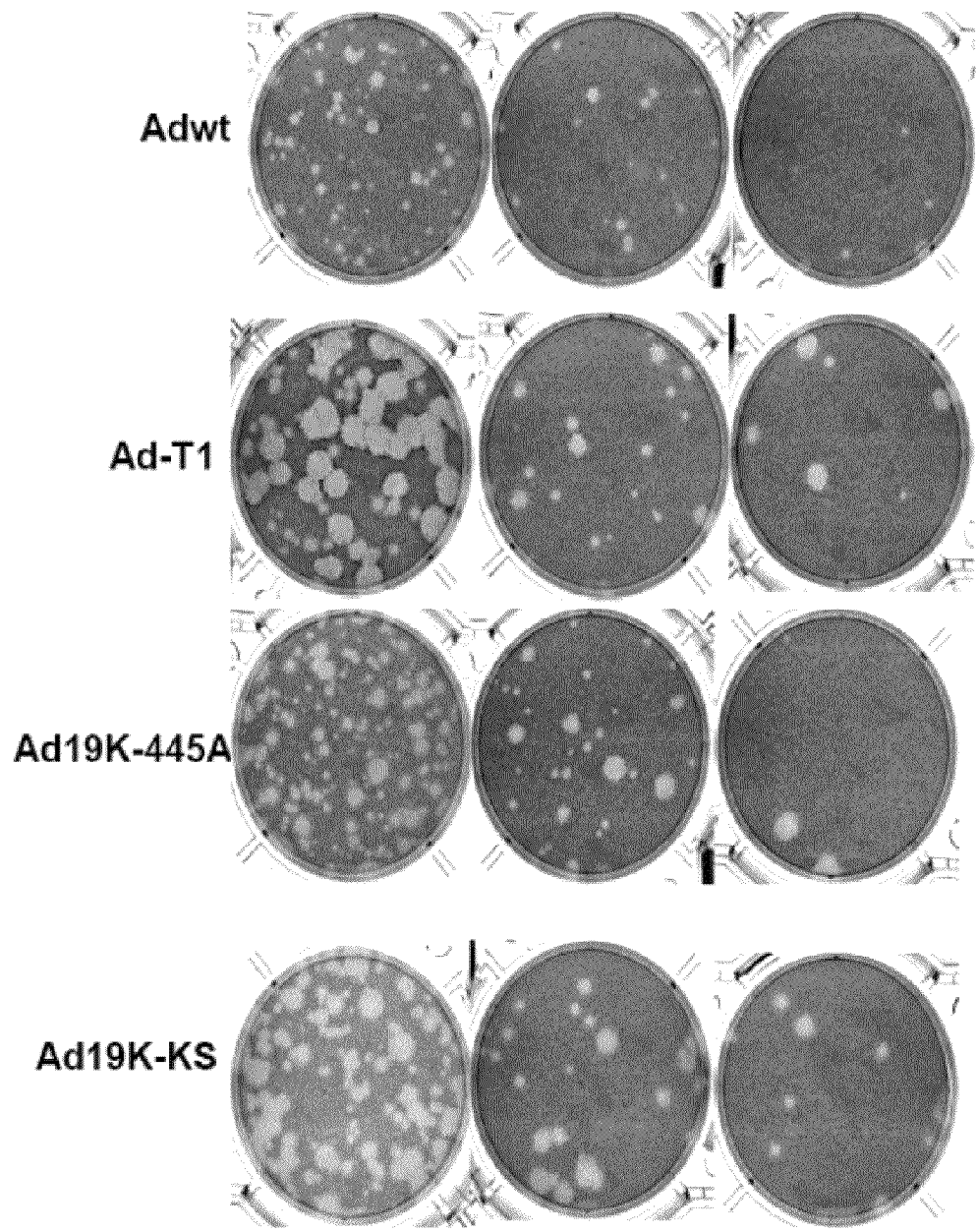
FIG. 6. Large plaque phenotype transfer to wild type adenovirus mediated by the insertion of the 445-A mutation of the endoplasmic reticulum retention domain of E3-19K. The 445-A mutation present in AdT1 was transferred to the wild type virus (Adwt) using yeast homologous recombination techniques to obtain the adenovirus Ad19K-445A. We also constructed another adenovirus mutant containing an independent mutation that eliminates the endoplasmic reticulum retention signal of E3-19K, the adenovirus Ad19K-KS, where the two lysines of the signal (KK) that are responsible for the retention of E3-19K in the endoplasmic reticulum, were substituted for two serines (SS) (SEQ ID NO: 4 and SEQ ID NO: 5). The plaque size of AdT1, Ad19K-445A, and Ad19K-KS was compared in a plaque assay. The three viruses showed a large plaque phenotype.

Mutation 445-A present in adenovirus AdT1 affects the endoplasmic reticulum retention domain of E3-19K and results in the large-plaque phenotype which indicates and improved cell-to-cell viral spread. To demonstrate that this phenotype is associated to a change in the localization of the E3-19K protein from the endoplasmic reticulum to the cell membrane and not to the specific 445-A mutation with no association with the change in localization, another virus was constructed with a mutation that differed from 445-A, but that also affected the endoplasmic reticulum retention domain of the E3-19K protein. This adenovirus called Ad19K-KS is characterized by the substitution of two lysines of the endoplasmic reticulum retention domain of E3-19K for two serines (SEQ ID NO: 4 and SEQ ID NO: 5). This modification in E3-19K, when studying the isolated protein, has been described to eliminate the retention of E3-19K in the endoplasmic reticulum (Pahl H L, Sester M, Burgert H G, Baeuerle P A. Activation of transcription factor NF-kappaB by the adenovirus E3/19K protein requires its ER retention. J Cell Biol 1996; 132(4):511-22). As shown in FIG. 6 of this invention the adenovirus constructed (Ad19K-KS) also presents a large-plaque phenotype. This result demonstrates that different mutations which affect the endoplasmic reticulum localization of E3-19K result in an enhanced viral spread.

Figure 7:
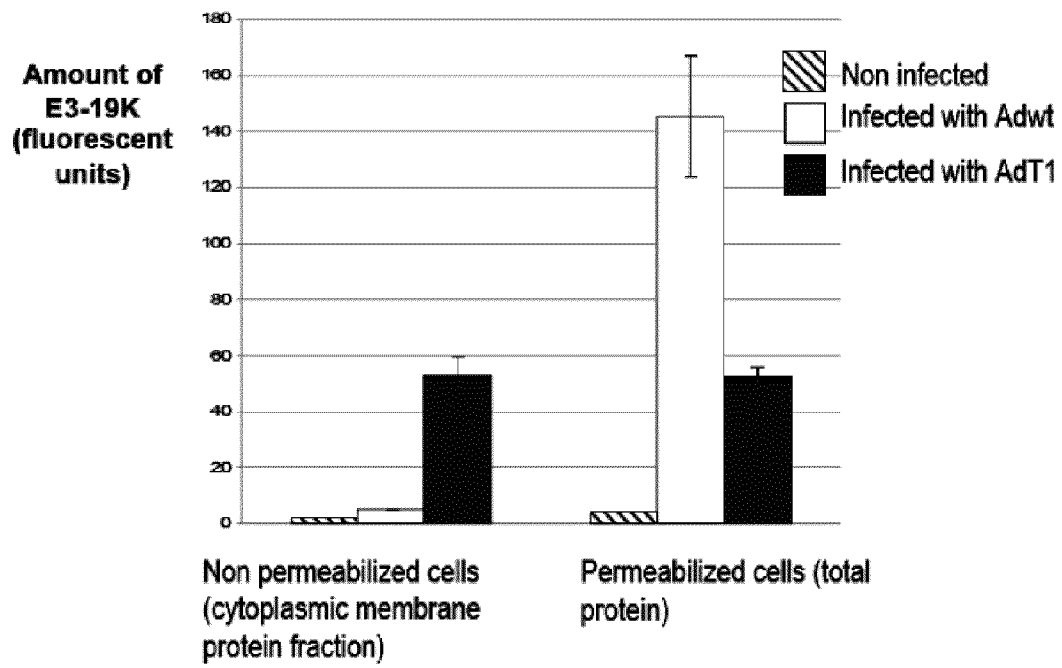
FIG. 7. Effect of the mutation in the endoplasmic reticulum retention domain of E3-19K on the cellular localization of E3-19K. To demonstrate that the inserted mutation changes the cellular localization of the adenovirus E3-19K protein, we infected a human tumor cell line (A549) with the same doses of Adwt and AdT1 (1500 virus particles/cell). Thirty-six hours post-infection cells were harvested and incubated in PBS or permeabilized with 70% ethanol. Then, cells were incubated with antibody Tw1.3 (anti-E3-19K) and this antibody was detected with a secondary antibody labelled with green fluorescent protein. Cell suspensions were passed through a flow cytometer and the mean value of three independent results is shown. In the absence of permeabilization of the plasma membrane, the E3-19K protein in detected only in cells infected with AdT1, indicating its exposure at the cell surface.
Figure 8:
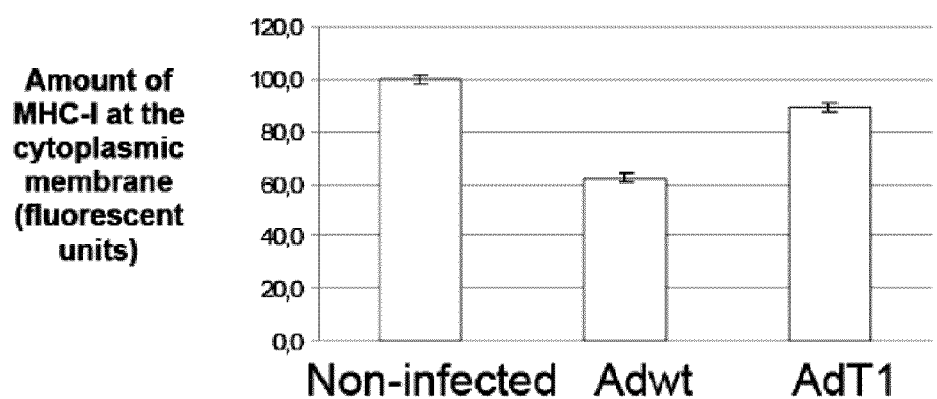
FIG. 8. Effect of the mutation in the endoplasmic reticulum retention domain of E3-19K on the cellular localization of MHC-I. To demonstrate that changes in the sub-cellular localization of the mutant form of E3-19K modify the exposure of the major histocompatibility complex class 1 (MHC-1) human tumor cells (A549) were infected with equivalent doses of Adwt or AdT1 (1500 virus particles/cell) and 24 hours post-infection cells were harvested. Next, cells were incubated with antibody W6/32 (against MHC-1) without permeabilization to exclusively label the MHC-1 fraction located at the plasma membrane. Bound W6/32 was then detected using a secondary antibody labelled with green fluorescent protein. Suspended cells were passed through a flow cytometer. The mean value of three independent analyses is shown. The MHC-I from the cells infected with AdT1 is exposed in the membrane to a similar lever as the MHC-I of non-infected cells and to a higher level than the MHC-I of cells infected with Adwt.
Figure 9:
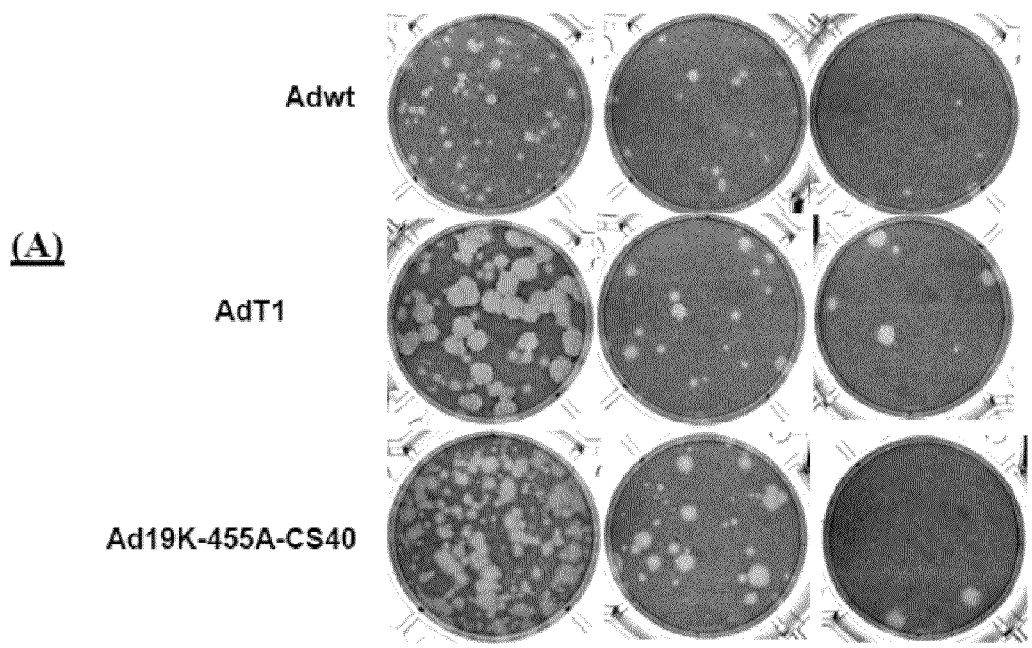
FIG. 9. Proof that the large plaque phenotype associated to the mutation in the endoplasmic reticulum retention domain of E3-19K does not depend on the function of MHC-I. In (A) we constructed an adenovirus named Ad19K-445A-CS40 containing the 445A mutation which removes the endoplasmic reticulum retention domain of E3-19K and also containing a mutation (CS40) that affects the MHC-I binding domain of E3-19K. Upon A549 infection, this mutant showed the same large plaque phenotype as AdT1 indicating that binding to MHC-I is not needed for this phenotype. The lower panel (B) shows a plaque assay of AdT1 in a cell line that lacks MHC-1 (DLD-1 cells, from human colon adenocarcinoma) and the large plaque phenotype is observed as well.

Since the main function of E3-19K is to bind to MHC I and retain MHC I at the endoplasmic reticulum preventing the immune response against the infected cell, the relationship between the phenotype of AdT1 and this function was studied. The infection with AdT1 which contains a mutation in the endoplasmic reticulum retention domain of E3-19K results in an increase of cell surface expression of E3-19K (FIG. 7). In parallel, there was an increase in the cell surface expression of MHC I when compared to cells infected with wild type adenovirus (FIG. 8). This change in localization of the E3-19K/MHC-I complex could be responsible for the large-plaque phenotype. To prove this hypothesis a virus containing both mutations 445-A of AdT1 and a mutation in the MHC I binding domain of E3-19K, named CS-40 (change of amino acid 40 of the native protein from cysteine to serine) was constructed. Virus Ad19K-445A-CS40 still presented a large-plaque phenotype (see FIG. 9) which indicates that the presence of the E3-19K/MHC I complex at the cell membrane was not necessary for the induction of the large-plaque phenotype. Further evidence confirming that MHC-I was not responsible for the large-plaque phenotype was the infection of DLD-1 cells with AdT1. Although these cells lacked cell surface MHC I expression AdT1 still presented larger plaques than Adwt (see FIG. 9).

Figure 10:
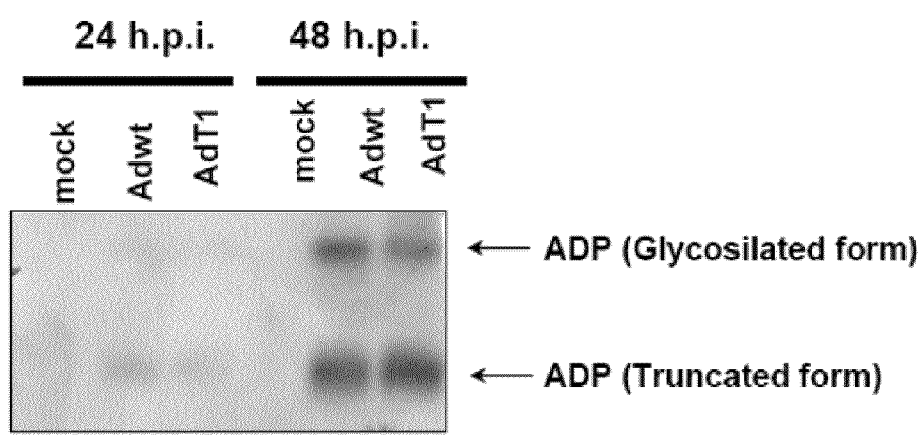
FIG. 10. Proof that the mutation in the endoplasmic reticulum retention domain of E3-19K does not result in adenovirus death protein (ADP) overexpression. We infected cells from the cell line A549 with Adwt or AdT1 (1500 virus particles/cell) and total cell protein was extracted at the indicated time points. As a control the same cells but without infection (mock) were used. An equivalent amount of protein extract of each sample (30 micrograms) was loaded on an acrylamide 15% gel to separate the proteins (SDS-PAGE). After running the gel, the proteins were transferred to a nitrocellulose filter (Western-blot procedure) and detected with an antibody against ADP. The result shows that AdT1 and Adwt express the same amount of ADP with the same kinetics.

Previously, ADP (E3-11.6K) overexpression has been described to result in a phenotype similar to the one presented in this invention. Adenoviruses with ADP overexpression are characterized by a large-plaque phenotype as a result of a more efficient and early viral release from the infected cell. The overexpression of ADP can be achieved by eliminating E3-19K and other E3 proteins thus enhancing the splicing of the E3-11.6K mRNA. To test if an adenovirus with a mutation in the endoplasmic reticulum retention domain of E3-19K, the object of this invention, results in the overexpression of ADP, which could explain the phenotype, ADP expression in AdT1-infected cells was determined. As observed in FIG. 10 of the invention, ADP detection by western-blot with an anti-ADP antibody indicated that the protein extracts of the AdT1-infected cells contained the same amount of ADP than the extracts of Adwt-infected cells and that it was expressed with similar kinetics. This demonstrates that the enhanced spread caused by the mutation in the endoplasmic reticulum retention domain of E3-19K did not depend on ADP overexpression and implies a new mechanism different from those previously described in the field of the invention.

In summary, this example illustrates that mutations in the endoplasmic reticulum retention domain of E3-19K result in an improved spread of adenovirus. Two different mutations, both affecting this domain, have the same effect which indicates the phenotype is associated to a change in the localization of E3-19K and not to the specific mutant sequence. The enhanced spread of adenoviruses with mutations in the endoplasmic reticulum retention domain of E3-19K does not depend on interaction with MHC I nor on ADP overexpression.

Example 2

Figure 11A:
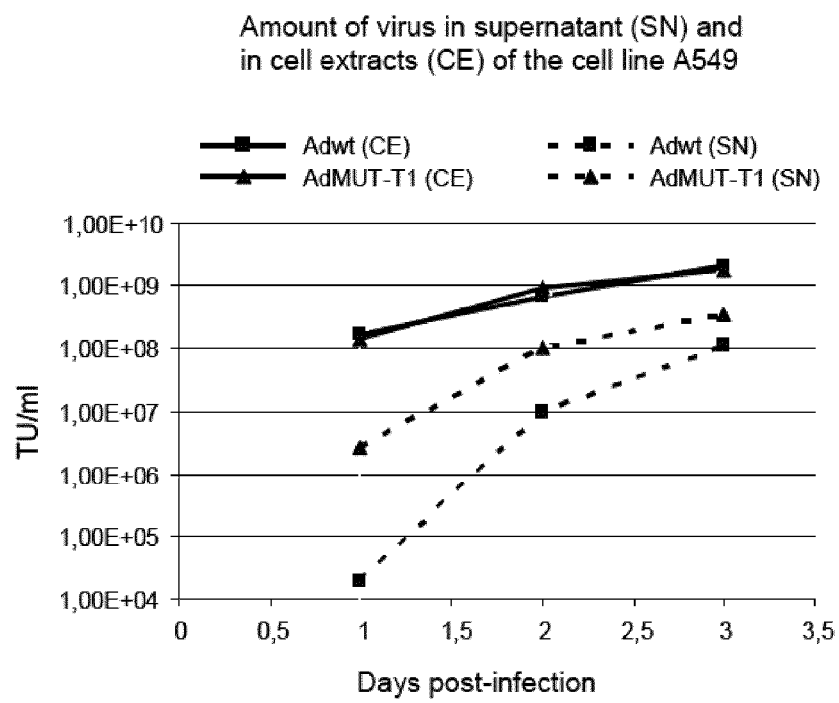
FIG. 11. Proof of higher release of virus to the supernatant of a cell infected with an adenovirus which contains a mutation in the endoplasmic reticulum retention domain of E3-19K. In (A) A549 cells were infected with Adwt or AdT1 (1500 virus particles/cell) and the amount of virus released to the supernatant or present in a cell extract (total virus) was measured at different time points. Whereas the total virus produced is the same for Adwt and AdT1, the AdT1 mutant is released more efficiently to the supernatant. The lower panel (B) shows the same experiment applied to several cell lines and represents the amount of virus detected in the supernatant of the infected cells at the indicated time points post-infection. In all the cell lines AdT1 is released more efficiently to the culture supernatant.
Figure 11B:
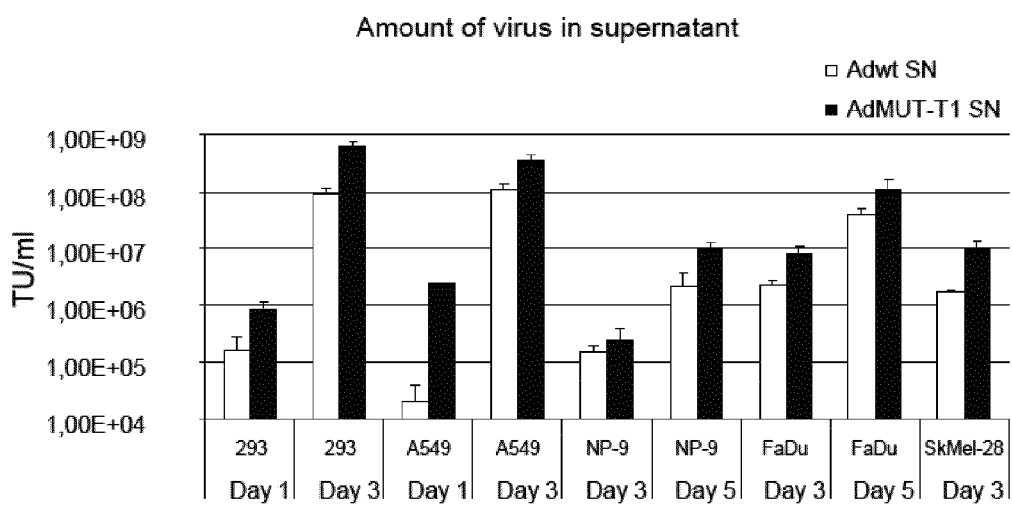
Figure 12:
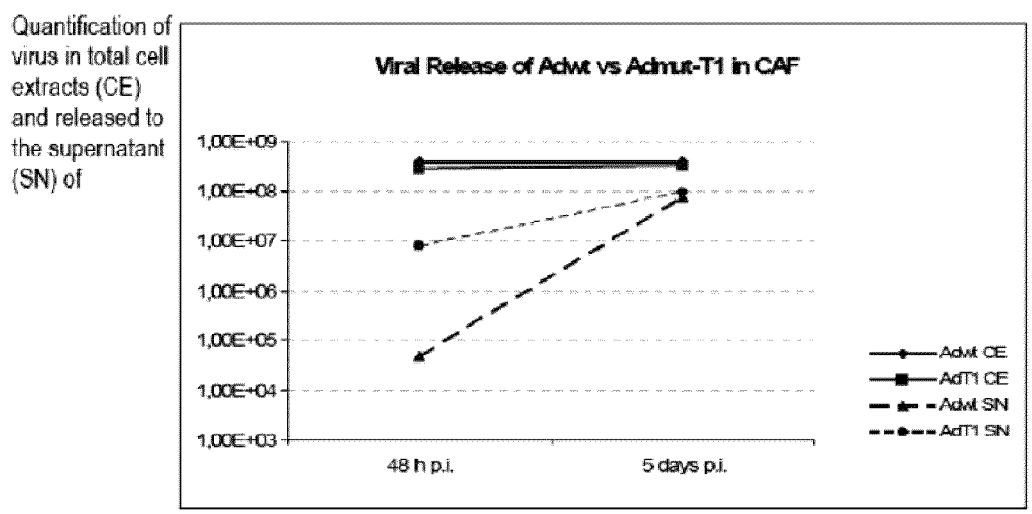
FIG. 12. Release of virus to the supernatant of a human fibroblast culture infected with an adenovirus which contains a mutation in the endoplasmic reticulum retention domain of E3-19K. Human fibroblasts were infected with Adwt or AdT1 (4500 virus particles/cell) and the amount of virus released to the supernatant or present in the cell extract (total virus) was measured at different time points. The result shows the higher release of virus AdT1 which contains a mutation in the endoplasmic reticulum retention domain of E3-19K.

An Adenovirus with Mutations in the Endoplasmic Reticulum Retention Domain of E3-19K is Released More Efficiently from the Infected Cells into the Supernatant The large-plaque phenotype discovered in Example 1 indicates an enhanced spread of adenoviruses with mutations in the endoplasmic reticulum retention domain of E3-19K. The plaque assay begins with a small number of infected cells and reflects the cell-to-cell spread of the virus as a result of several viral cycles. To determine if mutations in the endoplasmic reticulum retention domain of E3-19K produced an evident phenotypic change during the course of one viral cycle a monolayer of cells was infected with a large amount of AdT1 and the production and release of the viral progeny were compared to Adwt. To obtain information about the total viral production and release in one cycle of viral replication the intracellular virus and the virus present in the supernatant of the cell culture were measured separately. A monolayer of A549 cells in six-well plates was infected with 1500 viral particles per cell. The virus present in the supernatant and the cell extract was measured at different times post-infection. The result indicates that adenovirus AdT1, which contains a mutation in the endoplasmic reticulum retention domain of E3-19K, is released 100 times more efficiently than Adwt, while the total viral yield was unaffected (FIG. 11 of the invention, above). This assay was performed in a panel of tumor cell lines of different origin. AdT1 was released more efficiently than Adwt in all the cell lines tested (FIG. 11, below) and differences in viral release ranged from 5 to 125 times. To confirm if this phenotype of enhanced release into the supernatant was also evident in non tumor cells, human carcinoma-associated fibroblasts were isolated from human tumor biopsies. The result indicated that adenovirus AdT1 with mutations in the endoplasmic reticulum retention domain of E3-19K was also released more efficiently in these fibroblasts. In summary, this example demonstrates that a replication-competent adenovirus with mutations in the endoplasmic reticulum retention domain of E3-19K is released more efficiently from infected cells. The enhanced release of the virus from the infected cell is an appropriate characteristic of a replicating adenovirus for the treatment of cancer.

Example 3

Figure 13:
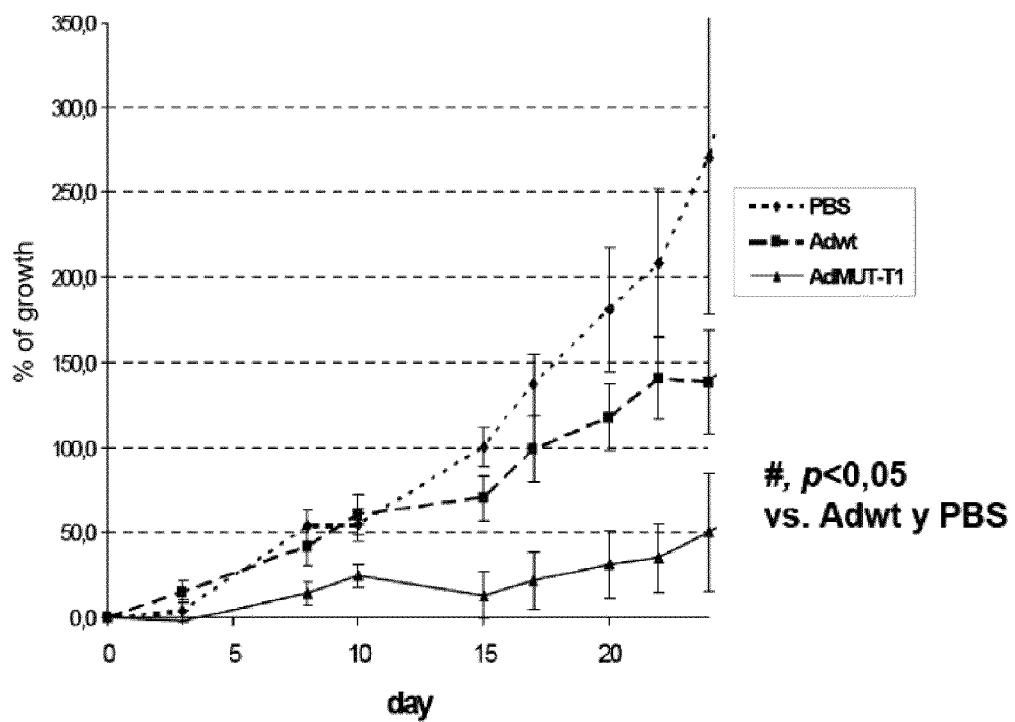
FIG. 13. Antitumor effect of an adenovirus which contains a mutation in the endoplasmic reticulum retention domain of E3-19K compared to a wild type adenovirus. Human pancreatic adenocarcinoma cells (NP-9) were inoculated subcutaneously in immune deficient mice (nude). When tumors developed, the mice were treated intravenously with $2.10^{10}$ virus particles/mouse of wild type adenovirus (Adwt) or mutant AdT1 adenovirus (10 mice/group) in a single dose. The percentage of tumor growth is shown as a function of time relative to day 0 (time of treatment). The result proves that the mutation in the endoplasmic reticulum retention domain of E3-19K increases the oncolytic potency of adenovirus.

The Mutation in the Endoplasmic Reticulum Retention Domain of E3-19K Enhances the Oncolytic Potency of Adenovirus and an Adenovirus with this Mutation can be Used to Treat Tumors Efficiently An in vivo experiment was performed in Balb/c nude mice harboring subcutaneous pancreatic human tumors. A total of $8 \times 10^6$ NP-9 cells were injected subcutaneously into the flanks of the mice. After 15 days when the tumor volumes reached 80-100 mm$^3$ the mice were randomized into the different experimental groups (n=10 per group). The control tumors were injected intravenously via tail vein with phosphate buffered saline (150 microliters). The group treated with AdT1 received a single intravenous injection of $2 \times 10^{10}$ viral particles/mouse. The tumors were measured every two days and the volume was calculated with formula: $V(mm^3) = A(mm)B^2(mm^2) \times 3,14/6$, where B is the length of the tumor. FIG. 13 shows the tumor growth since the day of injection (day 0). The results are presented as mean±S.E.M. The significance of the differences were calculated using a non-parametric Mann-Whitney test for unpaired samples. The growth curves were compared applying a variance analysis. The results were considered significant when p<0.05. The calculations were performed with SPSS statistical package (SPSS Inc., Chicago, Ill.). A significant difference was observed in the growth of the tumors treated with AdT1 since day 10 post-injection until the end of the experiment.

Example 4

Figure 14:
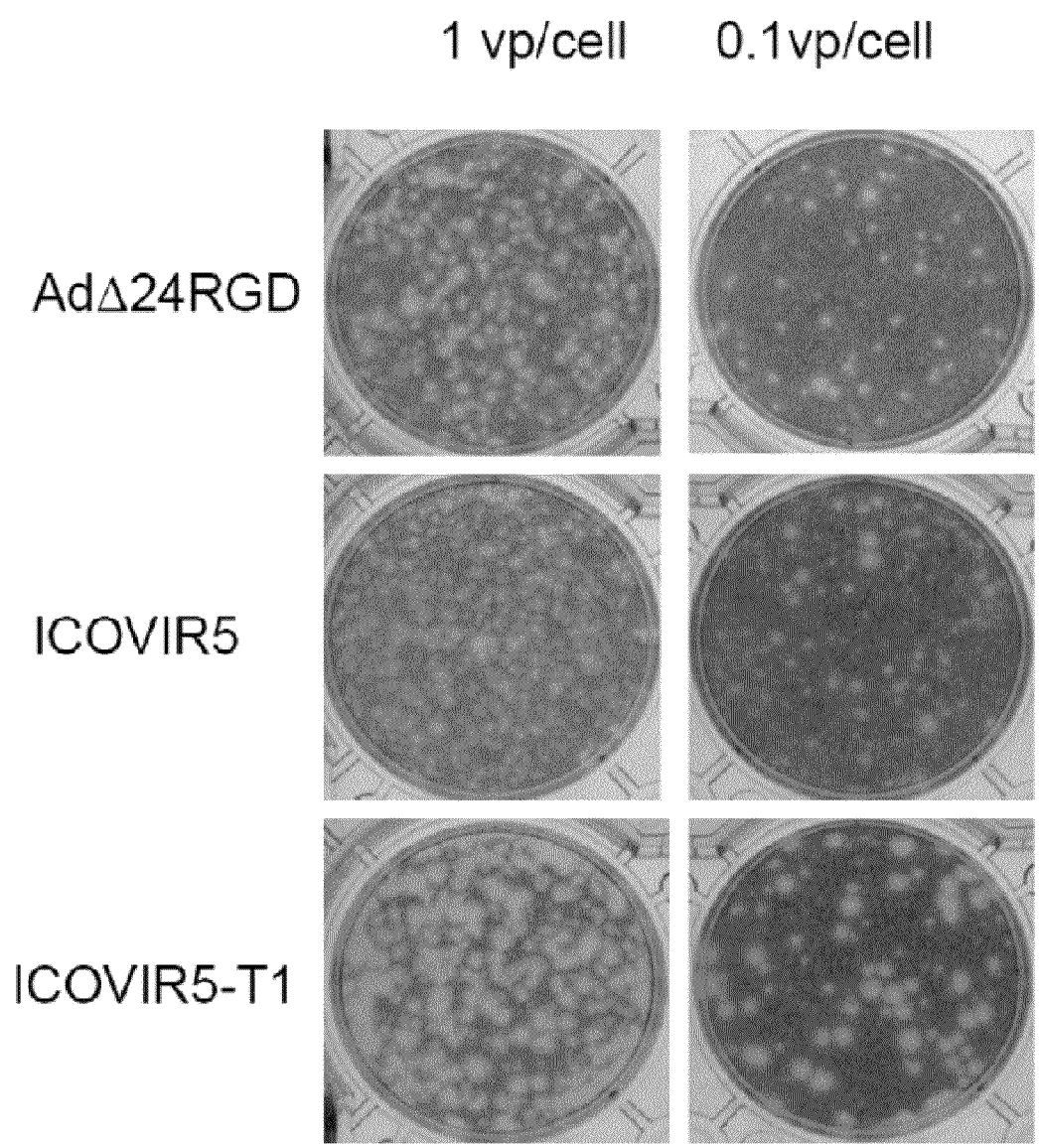
FIG. 14. Large plaque phenotype transfer to an oncolytic adenovirus mediated by the insertion of the 445-A (SEQ ID NO: 1 and SEQ ID NO:2) mutation of the endoplasmic reticulum retention domain of E3-19K. ICOVIR5 (as disclosed in CASCALLO M, ALONSO M M, ROJAS J J, PEREZ-GIMENEZ A, FUEYO J AND ALEMANY R. "Systemic Toxicity—Efficacy Profile of ICOVIR-5, a Potent and Selective Oncolytic Adenovirus Based on the pRB Pathway". Molecular Therapy. 2007 September; 15(9):1607-15) is an oncolytic adenovirus, which contains a mutation in the E1a gene (Δ24 mutation, delta-24 mutation, a deletion of nucleotides from 922 to 946 of AD5 that removes the pRB-binding site of E1a), an E2F1 promoter sequence to control the expression of such E1a-Δ24, the DM1 insulator, and the ccacc kozak sequence (all these mutations as defined by SEQ ID NO:7), and a capsid modification (RGD peptide insertion) to increase its infectivity towards tumor cells (mutation of SEQ ID NO:8). Positions from 1 to 366 of SEQ ID NO: 7 contain the ITR and packaging signal of the human adenovirus type (serotype) 5 (AY339865). In SEQ ID NO: 8, positions from 1 to 1638, and positions from 1666 to 1773, are codifying regions of the fiber of the human adenovirus type 5, corresponding, respectively, to the positions from nucleotide 31037 to 32674, and from nucleotide 32675 to 32782 of the AY339865. The 445-A mutation present in AdT1 was transferred to the oncolytic adenovirus ICOVIR5 using yeast homologous recombination techniques to obtain the adenovirus ICOVIR5-T1. AdΔ24RGD (as disclosed by SUZUKI, K., FUEYO, J. KRASNYKH, V., REYNOLDS, P., CURIEL, D. T., and ALEMANY, R. 2001. "A conditionally replicative adenovirus with enhanced infectivity shows improved oncolytic potency". Clinical Cancer Research-2001; 7(1): 120-126) is another adenovirus mutant containing the Δ24 and RGD mutations. The plaque size of ICOVIR5-T1, ICOVIR5 and AdΔ24RGD was compared in a plaque assay infecting a monolayer of A549 lung adenocarcinoma cells with 1 virus particle per cell (left panels) or 0.1 virus particle per cell (right panels) of ICOVIR5-T1, ICOVIR5 or AdΔ24RGD. After 10 days the plates we photographed. ICOVIR5-T1 showed a large plaque phenotype compared to ICOVIR5 and AdΔ24RGD.

An Oncolytic Conditionally-Replicative Adenovirus (ICOVIR5) with a Mutation in the Endoplasmic Reticulum Retention Domain of E3-19K Spreads More Efficiently ICOVIR5 (Cascallo et al. Molecular Therapy 15:1607. 2007) is a tumor-selective adenovirus which is mutated in the E1a gene (Δ24 mutation), contains an E2F1 promoter sequence to control the expression of such a mutated E1a (mutations reflected in SEQ ID NO: 7), and contains a capsid modification (RGD peptide insertion) to increase its infectivity towards tumor cells, as defined by SEQ ID NO: 8). To demonstrate that a mutation in the endoplasmic reticulum retention domain of E3-19K can be effectively combined with these genetic modifications characteristic of oncolytic adenoviruses, a derivative of ICOVIR5 containing the 445-A mutation in E3-19K (according to SEQ ID NO:1 and SEQ ID NO:2) was constructed and named ICOVIR5-T1. This virus was compared in a plaque assay to parental virus ICOVIR5, and to a second control virus with Δ24 and RGD mutations (named AdΔ24RGD). A plaque assay consists in the infection of a monolayer of tumor cells with a solution of diluted virus and the addition of an agar overlay after infection. Agar forms a jellifying polymer which prevents the spread of the virus throughout the culture and causes the virus to spread focally from the initially infected cells resulting in the formation of holes in the cell monolayer known as "plaques". A plaque assay was performed infecting a monolayer of A549 lung adenocarcinoma cells with 1 or 0.1 virus particle per cell of ICOVIR5-T1, ICOVIR5 or AdΔ24RGD. After 10 days the plates we photographed (FIG. 14 of the invention). The plaques of ICOVIR5-T1 were larger than the ICOVIR5 and AdΔ24RGD plaques.

Although the above mentioned examples illustrate adenoviruses with a mutation in the endoplasmic reticulum retention domain of E3-19K obtained from the serotype 5, the skilled man will understand that all the serotypes having the E3 genes and capable of translating the protein E3-19K are also the object of the present invention.

The invention claimed is:

1. A selectively replicating oncolytic adenovirus expressing an E3-19K protein having a mutation of its endoplasmic reticulum retention domain which prevents retention of the E3-19K protein in an animal cell endoplasmic reticulum, wherein the adenovirus comprises the E1a-Δ24 mutated adenovirus gene, wherein the E3-19K protein comprises a carboxy-terminus tail having an amino acid sequence of SEQ ID NO: 2.

2. The selectively replicating oncolytic adenovirus of claim 1, further comprising at least one gene selected from the group consisting of a prodrug-activating gene, a tumor-suppressor gene, or an immunostimulatory gene.

3. The selectively replicating oncolytic adenovirus of claim 1, wherein said adenovirus further comprises genome modifications that result in an enhancement of the expression of the E3-19K protein.

4. The selectively replicating oncolytic adenovirus of claim 1, wherein the mutant E3-19K protein comprises a carboxy-terminus tail encoded by the nucleotide sequence of SEQ ID NO: 1.

5. The selectively replicating oncolytic adenovirus of claim 1 in combination with one or more pharmaceutically acceptable carriers or excipients.

6. A method of making a pharmaceutical formulation for the treatment or prevention of cancer or the pre-malignant disease leading to cancer comprising combining the selectively replicating oncolytic adenovirus according to claim 1 with a pharmaceutically acceptable carrier or excipient.

7. The selectively replicating oncolytic adenovirus of claim 1, wherein the adenovirus further comprises a capsid modification to target it to a receptor present in a tumor cell, wherein the capsid modification is an RGD peptide insertion into the fiber protein.

8. The selectively replicating oncolytic adenovirus of claim 7 wherein the peptide insertion is SEQ ID NO:8.

9. The selectively replicating oncolytic adenovirus of claim 7, which is an adenovirus of group B, C, D or E.

10. The selectively replicating oncolytic adenovirus of claim 7, which is an adenovirus of serotype 5.

11. A selectively replicating oncolytic adenovirus expressing an E3-19K protein having a mutation of its endoplasmic reticulum retention domain which prevents retention of the E3-19K protein in an animal cell endoplasmic reticulum, wherein the adenovirus comprises the E1a-Δ24 mutated adenovirus gene, wherein the mutant E3-19K protein comprises a carboxy-terminus tail encoded by the nucleotide sequence of SEQ ID NO: 4.

12. A selectively replicating oncolytic adenovirus expressing an E3-19K protein having a mutation of its endoplasmic reticulum retention domain which prevents retention of the E3-19K protein in an animal cell endoplasmic reticulum, wherein the adenovirus comprises the E1a-Δ24 mutated adenovirus gene, wherein the mutant E3-19K protein comprises a carboxy-terminus tail having the amino acid sequence of SEQ ID NO: 5.

13. A selectively replicating oncolytic adenovirus expressing an E3-19K protein having a mutation of its endoplasmic reticulum retention domain which prevents retention of the E3-19K protein in an animal cell endoplasmic reticulum, wherein the adenovirus comprises the E1a-Δ24 mutated adenovirus gene, wherein the mutant E3-19K protein comprises a carboxy-terminus tail, comprising the amino acid sequence SEQ ID NO: 2 and the adenovirus comprises SEQ ID NO: 7 and the adenovirus further comprises SEQ ID NO: 8 encoding human adenovirus type 5 fiber protein with the arginine-glycine-asparagine (RGD) peptide.

14. The selectively replicating oncolytic adenovirus according to claim 13, wherein the mutant E3-19K comprises a carboxy-terminus tail encoded by the nucleotide sequence of SEQ ID NO: 1.

* * * * *